US012588823B2

(12) United States Patent
Wilson et al.

(10) Patent No.: US 12,588,823 B2
(45) Date of Patent: Mar. 31, 2026

(54) VIRTUALLY MONITORING BLOOD PRESSURE LEVELS IN A PATIENT USING MACHINE LEARNING AND DIGITAL TWIN TECHNOLOGY

(71) Applicant: Twin Health, Inc., Mountain View, CA (US)

(72) Inventors: James Wilson, Sunnyvale, CA (US); Frederick Hadley, Sunnyvale, CA (US); Terrence Chun Yin Poon, Foster City, CA (US); Jahangir Mohammed, Mountain View, CA (US)

(73) Assignee: Twin Health, Inc., Mountain View, CA (US)

( * ) Notice: Subject to any disclaimer, the term of this patent is extended or adjusted under 35 U.S.C. 154(b) by 1013 days.

(21) Appl. No.: 17/243,473

(22) Filed: Apr. 28, 2021

(65) Prior Publication Data

US 2022/0061676 A1      Mar. 3, 2022

Related U.S. Application Data

(60) Provisional application No. 63/073,880, filed on Sep. 2, 2020.

(51) Int. Cl.
*A61B 5/021* (2006.01)
*A61B 5/00* (2006.01)
(Continued)

(52) U.S. Cl.
CPC ............ *A61B 5/021* (2013.01); *A61B 5/7267* (2013.01); *A61B 5/7275* (2013.01); *A61B 5/742* (2013.01);
(Continued)

(58) Field of Classification Search
CPC ..... A61B 5/021; A61B 5/7267; A61B 5/7275; A61B 5/742; G16H 10/40; G16H 40/67; G16H 50/20; G16H 50/30; G16H 50/70
See application file for complete search history.

(56) References Cited

U.S. PATENT DOCUMENTS 10,319,477 B1      6/2019   Bill
11,185,283 B2 *   11/2021   Hadley ................ A61B 5/4833
                            (Continued)

FOREIGN PATENT DOCUMENTS

WO      WO 2016/038585 A1      3/2016
WO      WO 2017/019783 A1      2/2017
                            (Continued)

OTHER PUBLICATIONS

Chiang, Po-Han, and Sujit Dey. "Personalized effect of health behavior on blood pressure: Machine learning based prediction and recommendation." 2018 IEEE 20th International Conference on e-Health Networking, Applications and Services (Healthcom). IEEE, 2018. (Year: 2018).*
(Continued)

*Primary Examiner* — Jesse P Frumkin
(74) *Attorney, Agent, or Firm* — FENWICK & WEST LLP

(57) ABSTRACT

A patient health management platform implements a machine-learned metabolic model to generate a prediction of a patient's blood pressure. The platform implements a short-term prediction model to generate a daily prediction of the patient's blood pressure based on nutrition data reported by the patient and sensor data and lab test data collected for the patient. The platform implements a long-term prediction model generate a prediction of the patient's blood pressure during an extended time period based on sensor data and lab test data collected for the patient. Using the short-term prediction model, the long-term prediction model, or both,
(Continued)

the patient health management platform generates predictions of the patient's diastolic and systolic blood pressure and updates a digital twin of the patient's metabolic profile.

17 Claims, 10 Drawing Sheets

(51) Int. Cl.

| | |
|---|---|
| *G16H 10/40* | (2018.01) |
| *G16H 40/67* | (2018.01) |
| *G16H 50/20* | (2018.01) |
| *G16H 50/30* | (2018.01) |
| *G16H 50/70* | (2018.01) |

(52) U.S. Cl.
CPC ............. *G16H 10/40* (2018.01); *G16H 40/67* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 11,723,595 B2 * | 8/2023 | Hadley ................ | A61B 5/4833 600/365 |
| 2007/0055163 A1 | 3/2007 | Asada et al. | |
| 2015/0065826 A1 | 3/2015 | Mulligan et al. | |
| 2016/0140442 A1 | 5/2016 | Lee et al. | |
| 2017/0124450 A1 | 5/2017 | Hara et al. | |
| 2017/0215749 A1 | 8/2017 | Zhuo et al. | |
| 2017/0258340 A1 * | 9/2017 | Przybyszewski .. | A61B 5/02141 |
| 2017/0286622 A1 | 10/2017 | Cox et al. | |
| 2018/0116600 A1 * | 5/2018 | Basu ................... | A61B 5/0245 |
| 2018/0180633 A1 | 6/2018 | Volek et al. | |
| 2019/0209022 A1 | 7/2019 | Sobol et al. | |
| 2019/0252079 A1 | 8/2019 | Constantin et al. | |
| 2019/0307337 A1 | 10/2019 | Little et al. | |
| 2019/0307405 A1 | 10/2019 | Terry et al. | |
| 2019/0321553 A1 | 10/2019 | Grosman et al. | |
| 2020/0397972 A1 * | 12/2020 | Ku ......................... | G16H 50/70 |
| 2021/0045682 A1 * | 2/2021 | Poon ..................... | G16H 50/20 |
| 2021/0050089 A1 * | 2/2021 | Mohammed .......... | G06N 20/00 |
| 2021/0062734 A1 | 3/2021 | Fujinaka et al. | |
| 2021/0153750 A1 * | 5/2021 | Lu .......................... | A61B 5/021 |
| 2021/0244296 A1 * | 8/2021 | Huang ................... | G16H 50/70 |
| 2021/0282720 A1 * | 9/2021 | Soeseno ................ | G16H 50/20 |
| 2022/0338741 A1 * | 10/2022 | Schwager ............ | A61B 5/7285 |
| 2023/0337977 A1 * | 10/2023 | Hadley ................. | G16H 50/50 |
| 2024/0350098 A1 * | 10/2024 | Eun Young Yang .. | A61B 5/486 |

FOREIGN PATENT DOCUMENTS

| | | |
|---|---|---|
| WO | WO 2018/175935 A1 | 9/2018 |
| WO | WO 2018/232487 A1 | 12/2018 |

OTHER PUBLICATIONS

Su, Peng, et al. "Long-term blood pressure prediction with deep recurrent neural networks." 2018 IEEE EMBS International conference on biomedical & health informatics (BHI). IEEE, 2018. (Year: 2018).*

American Heart Association, Understanding Blood Pressure Readings, Retrieved online Jul. 15, 2021 from <https://www.heart.org/en/health-topics/high-blood-pressure/understanding-blood-pressure-readings>, four pages.

Bergenstal et al., "Glucose Management Indicator (GMI): A New Term for Estimating A1C From Continuous Glucose Monitoring," Diabetes Care Nov. 2018; 41(11): 2275-2280.

Stergion et al., "A Universal Standard for the Validation of Blood Pressure Measuring Devices," Hypertension, Mar. 2018, vol. 71, Issue 3, pp. 368-374.

Huttunen et al., Pulse transit time estimation of aortic pulse wave velocity and blood pressure using machine learning and simulated training data, *PLOS Computational Biology* 15.8 (2019): e1007259. Aug. 15, 2019 (Aug. 15, 2019) Retrieved on Jul. 19, 2021 (Jul. 19, 2021) from <https://journals.plos.org/ploscompbiol/article?id=10.1371/journal.pcbi.1007259>.

International Search Report and Written Opinion, Patent Cooperation Treaty Application No. PCT/US2021/029741, Aug. 3, 2021, 15 pages.

International Search Report and Written Opinion, Patent Cooperation Treaty Application No. PCT/US2021/029740, Sep. 27, 2021, 20 pages.

Indian Office Action, Intellectual Property India Patent Application No. 202347014766, mailing date Mar. 6, 2024, 8 pages.

United States Office Action, U.S. Appl. No. 17/243,470, Oct. 3, 2023, 100 pages.

United States Office Action, U.S. Appl. No. 17/243,470, Apr. 30, 2024, 24 pages.

European Patent Office, Extended European Search Report and Opinion, EP Patent Application No. 21864844.2, Sep. 19, 2024, 11 pages.

European Patent Office, Extended European Search Report and Opinion, EP Patent Application No. 21864845.9, Aug. 12, 2024, 11 pages.

United States Office Action, U.S. Appl. No. 17/243,470, Sep. 24, 2024, 24 pages.

Wu, T.H. et al., "Predicting Systolic Blood Pressure Using Machine Learning," IEEE, Dec. 22, 2014, pp. 1-6.

\* cited by examiner

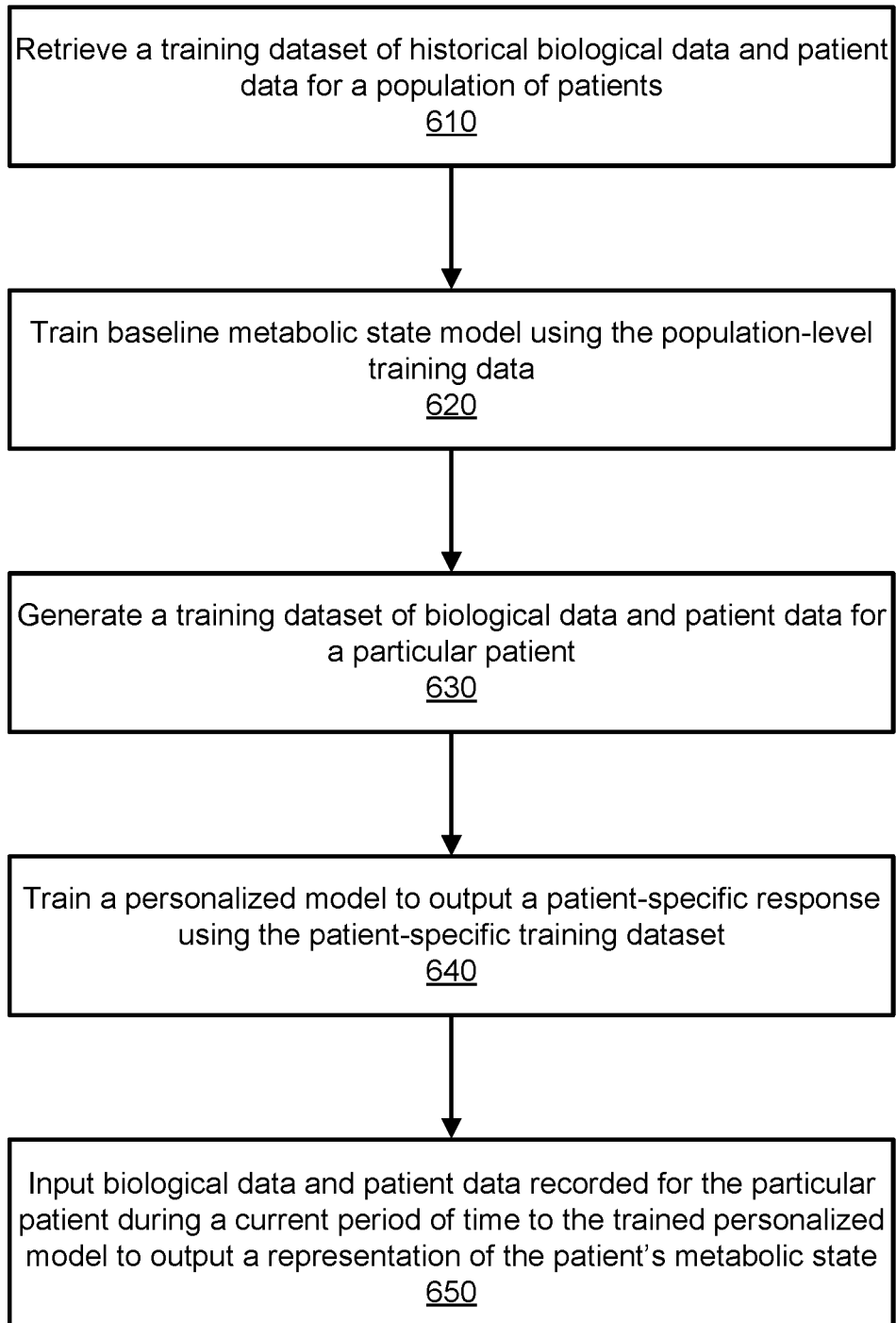

Retrieve a training dataset of historical biological data and patient data for a population of patients
610

Train baseline metabolic state model using the population-level training data
620

Generate a training dataset of biological data and patient data for a particular patient
630

Train a personalized model to output a patient-specific response using the patient-specific training dataset
640

Input biological data and patient data recorded for the particular patient during a current period of time to the trained personalized model to output a representation of the patient's metabolic state
650

FIG. 6

VIRTUALLY MONITORING BLOOD PRESSURE LEVELS IN A PATIENT USING MACHINE LEARNING AND DIGITAL TWIN TECHNOLOGY

CROSS REFERENCE TO RELATED APPLICATIONS

This application claims the benefit of U.S. Provisional Application No. 63/073,880, filed on Sep. 2, 2020, which is incorporated by reference in its entirety.

BACKGROUND

Field of Art

The disclosure relates generally to a patient health management platform, and more specifically, to a personalized treatment platform for virtually monitoring blood pressure levels in a patient using a machine-learned model and a collection of biosignals.

Description of the Related Art

Metabolic dysfunction, for example the metabolic dysfunction that occurs in type 2 diabetes, hypertension, lipid problems, heart disease, non-alcoholic fatty liver disease, polycystic ovarian syndrome, cancer, and dementia, is a major contributor to health care costs. Conventional disease management platforms or techniques either ignore or fail to fully understand important markers, such as blood sugar dysregulation, and root causes for these diseases, such as processed foods and a lack of exercise. Traditionally, these platforms are designed to treat symptoms as they arise rather than treating the root cause of the disease—the deterioration of a patient's metabolic health.

Regular monitoring of blood pressure levels is important to both manage and treat a patient's heart-related metabolic conditions, such as hypertension and heart disease. Such platforms often implement one or more of three classes of technologies: manual blood pressure meters (MBPM) s, digital blood pressure meters (DBPM), and ambulatory blood pressure meters (ABPM). Each of these conventional technologies inconveniences patients by causing discomfort, which makes these technologies unsuitable for long-term blood pressure monitoring. MBPM's require the patient to visit a clinic where they have to engage in a regular routine of applying a cuff and waiting 30-60 seconds for the reading to be taken. Newer wristwatch-based technologies or DBPM's, are more convenient to wear but still require the patient to hold an arm at heart level and to manually trigger the reading. ABPM's also require a patient to wear a cuff and, although the readings are automatic, patients typically do not wear them for more than 24 hours because the inflation/deflation sequences are uncomfortable and noisy, and can sometimes wake up patients at night. Additionally, these conventional technologies require active participation from patients, making it difficult to maintain in the long-term and contributing to low patient adherence (e.g., intermittent missed readings, periods of no usage during travel/vacation, etc.). Finally, the accuracy of the blood pressure measurements taken by these conventional technologies varies based on multiple manual factors. A measurement taken by an MBPM requires a manual judgement with each reading, whereas a measurement taken by a DBPM requires a patient to wear the cuff in a specific position on the arm/wrist and to hold the arm in a specific, stationary position during the reading. A measurement taken by an ABPM requires the patient to maintain the correct cuff positioning over 24 hours, throughout all the activities of the day. If any of these steps are not done accurately, the blood pressure measurements will likely be inaccurate.

SUMMARY

A patient health management platform for managing a patient's metabolic diseases generates a precision treatment using machine learning techniques and analyzing a unique combination of continuous biosignals (or near continuous or regularly collected biosignals). The platform performs various analyses to establish a personalized metabolic profile for each patient by gaining a deep understanding of how the combination of continuous biosignals impact the patient's metabolic health. These biosignals are input into machine-learned model(s) that recommend personalized treatment based on a unique metabolic profile of the patient. The machine-learned model(s) are trained to predict a patient's response to input biosignals at different stages of his or her treatment. Based on the output of the machine-learned model, the patient health management platform generates personalized recommendations for a patient outlining a treatment plan for improving the patient's metabolic health. To confirm that a patient-specific recommendation effectively addresses a patient's metabolic health, the patient health management evaluates the patient data recorded by a patient to confirm the timeliness, accuracy, and completeness of the recorded data.

One of the machine-learned models implemented by the patient health management platform is a virtual blood pressure monitor that is trained to output a prediction of patient's blood pressure. To generate the virtual blood pressure monitor, baseline metabolic model is trained to predict blood pressure on a population-level based on historical data collected from many (e.g., hundreds or thousands) of patients. For a particular patient, the baseline metabolic model is further trained based on patient-specific biosignals to generate a daily or regular estimation of the patient's blood pressure. Based on trends in a patient's heart rate measurements and exercise data recorded by a wearable sensor, the trained patient-specific virtual blood pressure monitor generates an estimation of a patient's blood pressure.

BRIEF DESCRIPTION OF DRAWINGS

FIG. 6 is a flowchart illustrating a process for training a machine-learned model to output a representation of a patient's metabolic health, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
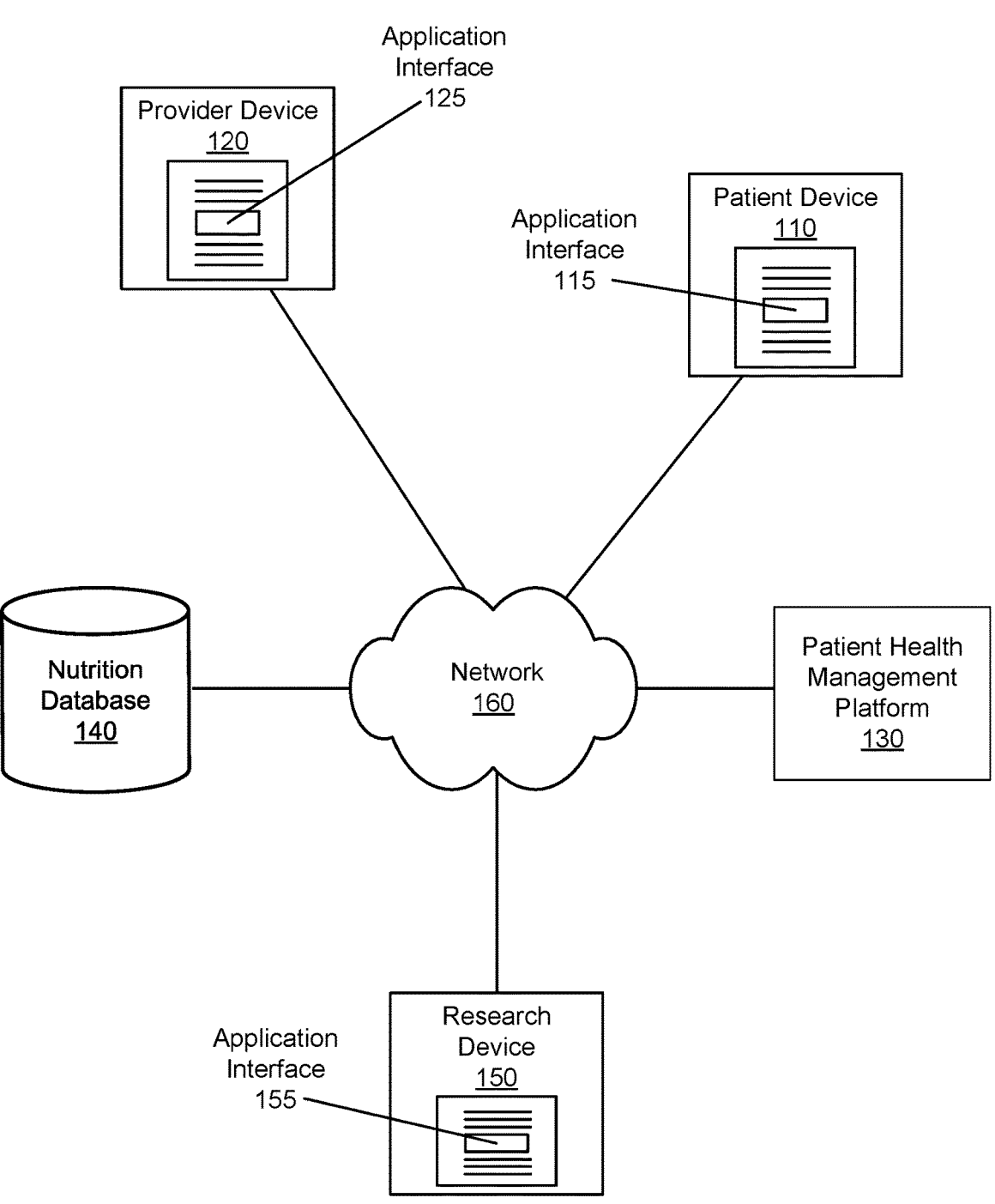
FIG. 1 shows a metabolic health manager for monitoring metabolic health of a patient, performing analytics on the metabolic health data, and providing a patient-specific recommendation for treating metabolic health-related concerns, according to one embodiment.

FIG. 1 shows a metabolic health manager 100 for monitoring a patient's metabolic health, for performing analytics on metabolic health data recorded for the patient, and for generating a patient-specific recommendation for treating any metabolic health-related concerns, according to one embodiment. The metabolic health manager 100 includes patient device(s) 110, provider device(s) 120, a patient health management platform 130, a nutrition database 140, research device(s) 150 and a network 160. However, in other embodiments, the system 100 may include different and/or additional components. For example, the patient device 110 can represent thousands or millions of devices for patients (e.g., patient mobile devices) that interact with the system in locations around the world. Similarly, the provider device 120 can represent thousands or millions of devices of providers (e.g., mobile phones, laptop computers, in-provider-office recording devices, etc.). In some cases, a single provider may have more than one device that interacts with the platform 130.

The patient device 110 is a computing device with data processing and data communication capabilities that is capable of receiving inputs from a patient. An example physical implementation is described more completely below with respect to FIG. 2. In addition to data processing, the patient device 110 may include functionality that allows the device 110 to record speech responses articulated by a patient operating the device (e.g., a microphone), and to graphically present data to a patient (e.g., a graphics display). Examples of the patient device 110 include desktop computers, laptop computers, portable computers, GOOGLE HOME, AMAZON ECHO, etc. The patient device 110 may present information generated by the communication platform 130 via a mobile application configured to display and record patient responses. For example, through a software application interface 115, a patient may receive a recommendation or an update regarding their metabolic health.

Application 115 provides a user interface (herein referred to as a "patient dashboard") that is displayed on a screen of the patient device 110 and allows a patient to input commands to control the operation of the application 115. The patient dashboard enables patients to track and manage changes in a patient's metabolic health. For example, the dashboard allows patients to observe changes in their metabolic health over time, receive recommendation notifications, exchange messages about treatment with a health care provider, and so on. The application 115 may be coded as a web page, series of web pages, or content otherwise coded to render within an internet browser. The application 115 may also be coded as a proprietary application configured to operate on the native operating system of the patient device 110. In addition to providing the dashboard, application 115 may also perform some data processing on biological and food data locally using the resources of patient device 110 before sending the processed data through the network 150. Patient data sent through the network 150 is received by the patient health management platform 130 where it is analyzed and processed for storage and retrieval in conjunction with a database.

Similarly, a provider device 120 is a computing device with data processing and data communication capabilities that is capable of receiving input from a provider. The provider device 120 is configured to present a patient's medical history or medically relevant data (i.e., a display screen). The above description of the functionality of the patient device 110 also can apply to the provider device 120. The provider device 120 can be a personal device (e.g., phone, tablet) of the provider, a medical institution computer (e.g., a desktop computer of a hospital or medical facility), etc. In addition, the provider device 120 can include a device that sits within the provider office such that the patient can interact with the device inside the office. In such implementations, the provider device is a customized device with audio and/or video capabilities (e.g., a microphone for recording, a display screen for text and/or video, an interactive user interface, a network interface, etc.). The provider device 120 may also present information to medical providers or healthcare organizations via a mobile application similar to the application described with reference to patient device 110.

Application 125 provides a user interface (herein referred to as a "provider dashboard") that is displayed on a screen of the provider device 120 and allows a medical provider or trained professional/coach to input commands to control the operation of the application 125. The provider dashboard enables providers to track and manage changes in a patient's metabolic health. The application 125 may be coded as a web page, series of web pages, or content otherwise coded to render within an internet browser. The application 125 may also be coded as a proprietary application configured to operate on the native operating system of the patient device 110.

The patient health management platform 130 is a medium for dynamically generating recommendations for improving a patient's metabolic health based on biological data recorded from a plurality of sources including wearable sensors (or other types of IoT sensors), lab tests, etc., and food or diet-related data recorded by the patient. The patient health management platform 130 predicts a patient's metabolic response based on periodically recorded patient data (e.g., nutrition data, symptom data, lifestyle data). Accordingly, a patient's metabolic response describes a change in metabolic health for a patient resulting from the food they most recently consumed and their current metabolic health. Based on such a change, the platform 130 generates a recommendation including instructions for a patient to improve their metabolic health or to maintain their improved metabolic health. Additionally, in real-time or near real-time, the patient health management platform 130 may provide feedback to a patient identifying potential inconsistencies or errors in the food or biological data entered manually by the patient based on a comparison of the patient's true metabolic state and their predicted metabolic state.

The nutrition database 140 stores nutrition data extracted from a collection of nutrient sources, for example food or vitamins. Data within the nutrition database 140 may be populated using data recorded by a combination of public sources and third-party entities such as the USDA, research programs, or affiliated restaurants. The stored data may include, but is not limited to, nutrition information (for example, calories, macromolecule measurements, vitamin concentrations, cholesterol measurements, or other facts) for individual foods or types of foods and relationships between foods and metabolic responses (for example, an impact of a given food on insulin sensitivity). Data stored in the nutrition database 140 may be applicable to an entire population (i.e., general nutrition information) or personalized to an individual patient (i.e., a personalized layer of the nutrition database). For example, the nutrition database 140 may store information describing a patient's particular biological (i.e., metabolic) response to a food. In such embodiments, the nutrition database 140 may be updated based on feedback from the patient health management platform 140.

Application 155 provides a user interface (herein referred to as a "research dashboard") that is displayed on a screen of the research device 150 and allows a researcher to input commands to control the operation of the application 155. The research dashboard enables providers to track and manage changes in a patient's metabolic health. The application 155 may be coded as a web page, series of web pages, or content otherwise coded to render within an internet browser. The application 155 may also be coded as a proprietary application configured to operate on the native operating system of the patient device 110.

Interactions between the patient device 110, the provider device 120, the patient health management platform 130, and the nutrition database 140 are typically performed via the network 150, which enables communication between the patient device 120, the provider device 130, and the patient communication platform 130. In one embodiment, the network 150 uses standard communication technologies and/or protocols including, but not limited to, links using technologies such as Ethernet, 802.11, worldwide interoperability for microwave access (WiMAX), 3G, 4G, LTE, digital subscriber line (DSL), asynchronous transfer mode (ATM), InfiniBand, and PCI Express Advanced Switching. The network 150 may also utilize dedicated, custom, or private communication links. The network 150 may comprise any combination of local area and/or wide area networks, using both wired and wireless communication systems.

Figure 2:
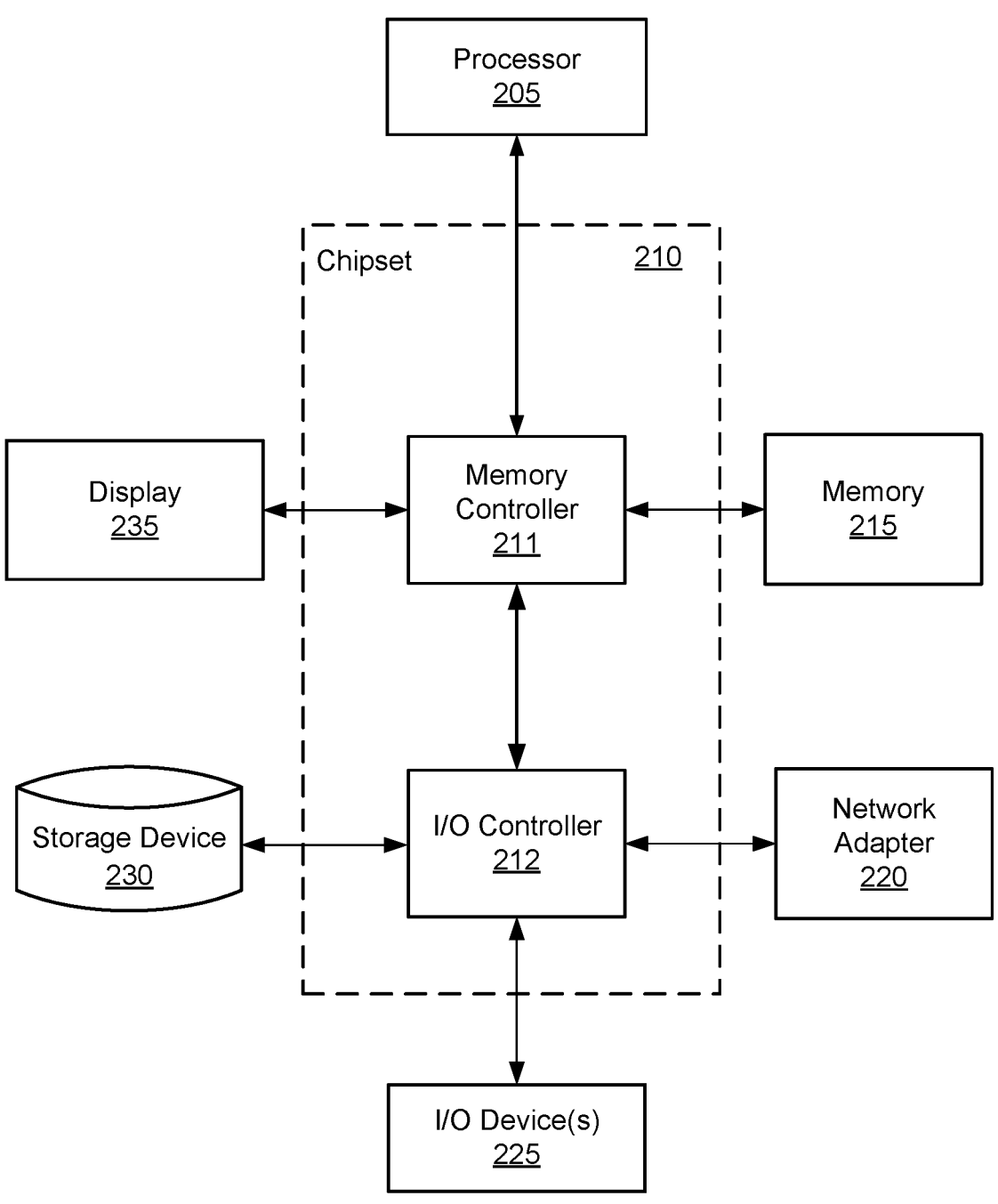
FIG. 2 is a high-level block illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

II. Over View of Metabolic Health Manager

In the United States, treating non-communicable diseases including, but not limited to, diabetes, hyper-tension, high-cholesterol, heart disease, obesity, fatty liver disease, arthritis, irritable bowel syndrome (IBS), and infertility, is a multi-billion-dollar industry. Still, these diseases account for over 2 million deaths annually. Conventional treatments are directed towards addressing and alleviating symptoms of each disease, but fail to recognize that the root of all the aforementioned diseases is an impaired metabolism. By addressing root cause metabolic impairments, a patient's disease may not just be managed on a per symptom basis, but reversed entirely. Accordingly, a treatment or system for generating a treatment directed towards treating metabolic impairments in patients suffering from such diseases could be more effective and most cost-efficient. Because the patient health management platform 100 aims to treat a patient's metabolic impairments, a patient using the patient health management platform 100 for an extended time period may transition from a first state of impaired metabolism to a second state of functional metabolism to a third state of optimal metabolism.

The patient health management platform 130, as described herein, recognizes that a patient's body is a unique system in a unique state in which metabolism is a core biochemical process. Accordingly, the treatment and nutrition recommendations generated by the platform 130 are tailored to suit a patient's unique metabolic state and the unique parameters or conditions that impact or have previously impacted their metabolic state. To enable a patient to achieve good or optimal metabolic health, the platform 130 records measurements of various factors and aims to improve these measurements to levels representative of an optimized metabolic state. For example, five factors commonly considered include blood sugar, triglycerides, good cholesterol (high-density lipoprotein), blood pressure, and waist circumference. Each human body is different and continuously evolving. To guide a patient towards optimal metabolic health, the platform establishes a deep understanding of the dynamic states of each human body over time by capturing continuous biosignals and deriving insights from these biosignals.

For each patient, the platform 130 leverages a combination of personalized treatments that are tailored to a patient's unique metabolic state based on a combination of timely, accurate, and complete recordings of metabolic biosignals. Such measurements are collectively referred to herein as "TAC measurements." The platform determines a current metabolic state of a human body by analyzing a unique combination of continuous biosignals received from various sources including, but not limited to, near-real-time data from wearable sensors (e.g. continuous blood glucose, heart rate, etc.), periodic lab tests (e.g., blood work), nutrition data (e.g., macronutrients, micronutrients, and biota nutrients from food and supplements of the patient), medicine data (e.g., precise dosage and time of medications taken by the patient), and symptom data (e.g., headache, cramps, frequent urination, mood, energy, etc., reported by each patient via a mobile app). This analysis is performed continuously to establish a time series of metabolic states. As a result, the platform understands not only the current state of each patient, but also the full history of states that led to the current state. Using a patient's current metabolic state and their full history of metabolic states, the platform is able to deeply personalize the treatment for each patient.

The platform applies various technologies and processing techniques to gain a deep understanding of the combination of factors contributing to a patient's metabolic state and to establish a personalized metabolic profile for each patient. For example, the platform implements a combination of analytics (e.g., analyzing trends, outliers, and anomalies in biosignals as well as correlations across multiple biosignals), rule based artificial intelligence (AI), machine learning-based AI, and automated cohorting or clustering.

For the sake of explanation, the concepts and techniques described herein are described with reference to diabetes. However, one of skill in the art would recognize that the concepts and techniques may also be applied to any other disease resulting from an impaired metabolism. As will be described herein, a patient's metabolic health describes the overall effectiveness of their metabolism. For example, a patient's metabolic health may be categorized as impaired, functional, or optimal. To gain insight into a patient's metabolic health, the patient health management platform 130 identifies metabolic states occurring over a time period and changes between those metabolic states. As described herein, a metabolic state represents a patient's state of metabolic health at a specific time (e.g., a state of metabolic health resulting from consumption of a particular food or adherence to a particular medication/treatment).

In addition, the term "continuously" is used throughout the description to characterize the collection of biosignals and other data regarding the patient. This term can refer to a rate of collection that is truly continuous (e.g., a constantly recorded value) or near continuous (e.g., collection at every time point or time increment, such as every millisecond, second, or minute), such as biosignals recorded by a wearable device. In some cases, continuously recorded data may refer to particular biosignals that occur semi-regularly, such as a lab test that is taken at a recurring time interval (e.g., every 10 minutes, 30 minutes, hour, 5 hours, day or number of days, week or number of weeks, etc.). The term "continuously" does not exclude situations in which wearable sensors may be removed during certain activities or at times of day (e.g., while showering). In other embodiments, the platform collects multiple biosignals that, in combination, represent a continuous or near continuous signal collection even though some biosignals are collected more frequently than others.

The approved treatment recommendation is communicated to a patient device 110, which presents the recommendation to a patient via the patient health management application. By interacting with the patient health management application, the patient reviews the treatment recommendation, tracks their progress through the treatment recommendation, and receives notifications generated by the platform regarding changes in their metabolic health. In some implementations, the patient health management application may receive information from the patient health management platform identifying inconsistencies or errors in information recorded using the application and request that the patient correct the identified errors. Examples of such identified errors include, but are not limited to, incorrectly recording the time at which food or medication was consumed, incorrectly recording the amount of food or medication consumed, forgetting to record that a food or medication was consumed, or incorrectly recording which food or medication was consumed.

III. Biosignal Data

A patient health management platform receives biosignal data for a patient from a variety of sources including, but not limited to, wearable sensor data, lab test data, nutrition data, medication data, symptom data.

A patient using the metabolic health manager is outfitted with one or more wearable sensors configured to continuously record biosignals, herein referred to as wearable sensor data. Wearable sensor data includes, but is not limited to, biosignals describing a patient's heart rate, record of exercise (e.g., steps, average number of active minutes), quality of sleep (e.g., sleep duration, sleep stages), a blood glucose measurement, a ketone measurement, systolic and diastolic blood pressure measurements, weight, BMI, percentage of fat, percentage of muscle, bone mass measurement, and percent composition of water. A wearable sensor may be a sensor that is periodically removable by a patient (e.g., a piece of jewelry worn in contact with a patient's skin to record such biosignals) or a non-removable device/sensor embedded into a patient's skin (e.g., a glucose patch). Whenever worn or activated to record wearable sensor data, the sensor continuously records one or more of the measurements listed above. In some implementations, a wearable sensor may record different types of wearable sensor data at different rates or intervals. For example, the wearable sensor may record blood glucose measurements, heart rate measurements, and steps in 15 second intervals, but record blood pressure measurements, weight measurements, and sleep trends in daily intervals.

The patient health management platform also receives lab test data recorded for a patient. As described herein, lab test data describes the results of lab tests performed on the patient. Examples of lab test data include, but are not limited to, blood tests or blood draw analysis. Compared to the frequencies at which wearable sensor data is recorded, lab test data may be recorded at longer intervals, for example bi-weekly or monthly. In some implementations, the patient health management platform receives data measured from 126-variable blood tests.

The patient health management platform may also receive nutrition data describing food that a patient is consuming or has consumed. Via an application interface presented on the patient device 110, a patient enters a record of food that they have consumed on a per meal basis and a time at which each item of food was consumed. Alternatively, the patient may enter the record for food on a daily basis. The patient health management platform extracts nutrition details (e.g., macronutrient, micronutrient, and biota nutrient data) from a nutrition database (not shown) based on the food record entered by the patient. As an example, via a patient device 110, a patient may record that they consumed two bananas for breakfast at 7:30 AM. The record of the two bananas is communicated to the patient health management platform 350 and the patient health management platform accesses, from a nutrition database, nutrient data including the amount of potassium in a single banana. The accessed nutrient data is returned to the patient health management platform as an update to the recorded nutrition data 320. Via the same interface or one similar to the interface used to record food consumed, a patient may record and communicate medication data and symptom data to the patient health management platform 350. Medication data 35 describes a type of medication taken, a time at which the medication was taken, and an amount of the medication taken. In addition to nutrition data and medication data, the patient health management platform may receive descriptions of a patient's energy, mood, or general level of satisfaction with their lifestyle, treatment plan, and disease management.

Examples of biosignal data recorded and communicated to the patient health management platform include, but are not limited to, those listed in Table 1. Table 1 also lists a source for recording each example of biosignal data.

TABLE 1

Example Biosignal Data and Source

| Category | Type | Signal | Source |
|---|---|---|---|
| Sensor Data | Biomarker | Weight | Body Composition Scale |
| | Biomarker | Body fat % | Body Composition Scale |
| | Biomarker | Subcutaneous fat % | Body Composition Scale |
| | Biomarker | Visceral fat % | Body Composition Scale |
| | Biomarker | Body water % | Body Composition Scale |

TABLE 1-continued

Example Biosignal Data and Source

| Category | Type | Signal | Source |
|---|---|---|---|
| | Biomarker | Muscle % | Body Composition Scale |
| | Biomarker | Bone mass | Body Composition Scale |
| | Biomarker | Basal metabolic rate | Body Composition Scale |
| | Biomarker | Protein | Body Composition Scale |
| | Biomarker | Lean body weight | Body Composition Scale |
| | Biomarker | Muscle mass | Body Composition Scale |
| | Biomarker | Metabolic age | Body Composition Scale |
| | Biomarker | Continuous Blood Glucose | Continuous Glucose Meter |
| | Biomarker | Ketones | Ketone Meter |
| | Biomarker | Systolic BP | Blood Pressure Meter |
| | Biomarker | Diastolic BP | Blood Pressure Meter |
| | Heart | Resting Heart Rate | Fitness Watch |
| | Heart | Continuous Heart Rate | Fitness Watch |
| Lab Test Data | Biomarker | Skin Temperature | Patient Investigation/ Test |
| | Biomarker | Oxygen Saturation | Patient Investigation/ Test |
| | Biomarker | Waist Circumference | Patient Investigation/ Test |
| | Biomarker | Age | Patient Interview |
| | Biomarker | Gender | Patient Interview |
| | Biomarker | Height | Patient Interview |
| | Biomarker | BMI | Patient Interview |
| | Biomarker | HbA1c | Blood Test |
| | Biomarker | 5dg-cgm | Blood Test |
| | Biomarker | 1dg-cgm | Blood Test |
| | Biomarker | Insulin | Blood Test |
| | Biomarker | Fructosamine | Blood Test |
| | Biomarker | C-Peptide | Blood Test |
| | Biomarker | HOMA-IR | Blood Test |
| | Biomarker | 5dk | Blood Test |
| | Biomarker | Cholesterol | Blood Test |
| | Biomarker | Triglycerides | Blood Test |
| | Biomarker | HDL Cholesterol | Blood Test |
| | Biomarker | LDL Cholesterol | Blood Test |
| | Biomarker | VLDL Cholesterol | Blood Test |
| | Biomarker | Triglyceride/ HDL Ratio | Blood Test |
| | Biomarker | Total Cholesterol/ HDL Ratio | Blood Test |
| | Biomarker | Non-HDL Cholesterol | Blood Test |
| | Biomarker | LDL/HDL Ratio | Blood Test |
| | Biomarker | Total Iron Binding Capacity (TIBC) | Blood Test |
| | Biomarker | Serum Iron | Blood Test |
| | Biomarker | % Transferrin Saturation | Blood Test |
| | Biomarker | Amylase | Blood Test |
| | Biomarker | Lipase | Blood Test |
| | Biomarker | Ferritin | Blood Test |
| | Biomarker | Homocysteine | Blood Test |
| | Biomarker | Magnesium | Blood Test |
| | Biomarker | ALT | Blood Test |
| | Biomarker | AST | Blood Test |
| | Biomarker | ALP | Blood Test |
| | Biomarker | Total Bilirubin | Blood Test |
| | Biomarker | Direct Bilirubin | Blood Test |
| | Biomarker | Indirect Bilirubin | Blood Test |
| | Biomarker | Gamma Glutamyl Transferase (GGT) | Blood Test |

TABLE 1-continued

Example Biosignal Data and Source

| Category | Type | Signal | Source |
|---|---|---|---|
| | Biomarker | Protein | Blood Test |
| | Biomarker | Albumin | Blood Test |
| | Biomarker | A/G Ratio | Blood Test |
| | Biomarker | Globulin | Blood Test |
| | Biomarker | Urea | Blood Test |
| | Biomarker | Creatinine | Blood Test |
| | Biomarker | Uric Acid | Blood Test |
| | Biomarker | GFR | Blood Test |
| | Biomarker | Blood urea nitrogen (BUN) | Blood Test |
| | Biomarker | BUN/Creatinine Ratio | Blood Test |
| | Biomarker | Lipoprotein(a) | Blood Test |
| | Biomarker | Apolipoprotein A1 | Blood Test |
| | Biomarker | ApoB | Blood Test |
| | Biomarker | hs-CRP | Blood Test |
| | Biomarker | Apo B/Apo A1 Ratio | Blood Test |
| | Biomarker | LP-PLA2 | Blood Test |
| | Biomarker | Total Tri-iodothyronine [T3] | Blood Test |
| | Biomarker | Total Thyroxine [T4] | Blood Test |
| | Biomarker | TSH | Blood Test |
| | Biomarker | Sodium | Blood Test |
| | Biomarker | Chloride | Blood Test |
| | Biomarker | Potassium | Blood Test |
| | Biomarker | Bicarbonate | Blood Test |
| | Biomarker | Calcium | Blood Test |
| | Biomarker | Phosphorous | Blood Test |
| | Biomarker | Anion Gap | Blood Test |
| | Biomarker | Vitamin A | Blood Test |
| | Biomarker | Vitamin D2 | Blood Test |
| | Biomarker | Vitamin D3 | Blood Test |
| | Biomarker | Vitamin D Total | Blood Test |
| | Biomarker | Vitamin E | Blood Test |
| | Biomarker | Vitamin K | Blood Test |
| | Biomarker | Vitamin B1/Thiamin | Blood Test |
| | Biomarker | Vitamin B2/Riboflavin | Blood Test |
| | Biomarker | Vitamin B3/Nicotinic Acid | Blood Test |
| | Biomarker | Vitamin B5/Pantothenic Acid | Blood Test |
| | Biomarker | Vitamin B6/Pyridoxal-5-Phosphate | Blood Test |
| | Biomarker | Vitamin B7/Biotin | Blood Test |
| | Biomarker | Vitamin B9/Folic Acid | Blood Test |
| | Biomarker | Vitamin B12/Cobalamin | Blood Test |
| | Biomarker | Cortisol | Blood Test |
| | Biomarker | Cystatin C | Blood Test |
| | Biomarker | Serum Zinc | Blood Test |
| | Biomarker | Serum Copper | Blood Test |
| | Biomarker | Basophils-Absolute Count | Blood Test |
| | Biomarker | Eosinophils-Absolute Count | Blood Test |
| | Biomarker | Lymphocytes-Absolute Count | Blood Test |
| | Biomarker | Monocytes-Absolute Count | Blood Test |
| | Biomarker | Mixed-Absolute Count | Blood Test |

TABLE 1-continued

Example Biosignal Data and Source

| Category | Type | Signal | Source |
|---|---|---|---|
| | Biomarker | Neutrophils-Absolute Count | Blood Test |
| | Biomarker | Basophils | Blood Test |
| | Biomarker | Eosinophils | Blood Test |
| | Biomarker | Immature Granulocytes (Ig) | Blood Test |
| | Biomarker | Immature Granulocyte Percentage (Ig %) | Blood Test |
| | Biomarker | White Blood Cells (Leucocytes Count) | Blood Test |
| | Biomarker | Lymphocyte Percentage | Blood Test |
| | Biomarker | Mean Corpuscular Hemoglobin (Mch) | Blood Test |
| | Biomarker | Mean Corp. Hemo. Conc. (Mchc) | Blood Test |
| | Biomarker | MCV | Blood Test |
| | Biomarker | Monocytes | Blood Test |
| | Biomarker | Mean Platelet Volume (Mpv) | Blood Test |
| | Biomarker | Neutrophils | Blood Test |
| | Biomarker | Nucleated Red Blood Cells | Blood Test |
| | Biomarker | Nucleated Red Blood Cells % | Blood Test |
| | Biomarker | Plateletcrit (Pct) | Blood Test |
| | Biomarker | Hematocrit | Blood Test |
| | Biomarker | Platelet Distribution Width (Pdw-SD) | Blood Test |
| | Biomarker | Platelet To Large Cell Ratio (Plcr) | Blood Test |
| | Biomarker | Platelet Count | Blood Test |
| | Biomarker | Red Blood Cell Count | Blood Test |
| | Biomarker | Red Cell Distribution Width (Rdw-Cv) | Blood Test |
| | Biomarker | Red Cell Distribution Width-Sd (Rdw-Sd) | Blood Test |
| | Biomarker | Blood pH | Blood Test |
| | Biomarker | Hemoglobin | Blood Test |
| | Biomarker | ACCP | Blood Test |
| | Biomarker | ANA | Blood Test |
| | Biomarker | Cadmium | Blood Test |
| | Biomarker | Cobalt | Blood Test |
| | Biomarker | Chromium | Blood Test |
| | Biomarker | Caesium | Blood Test |
| | Biomarker | Mercury | Blood Test |
| | Biomarker | Manganese | Blood Test |
| | Biomarker | Molybdenum | Blood Test |
| | Biomarker | Nickel | Blood Test |
| | Biomarker | Lead | Blood Test |
| | Biomarker | Antimony | Blood Test |
| | Biomarker | Selenium | Blood Test |
| | Biomarker | Tin | Blood Test |
| | Biomarker | Strontium | Blood Test |
| | Biomarker | Thallium | Blood Test |
| | Biomarker | Uranium | Blood Test |
| | Biomarker | Vanadium | Blood Test |
| | Biomarker | Silver | Blood Test |
| | Biomarker | Aluminium | Blood Test |

TABLE 1-continued

Example Biosignal Data and Source

| Category | Type | Signal | Source |
|---|---|---|---|
|  | Biomarker | Arsenic | Blood Test |
|  | Biomarker | Barium | Blood Test |
|  | Biomarker | Beryllium | Blood Test |
|  | Biomarker | Bismuth | Blood Test |
|  | Biomarker | Testosterone | Blood Test |
| Lifestyle Data | Sleep | Sleep Quality | Fitness Watch |
|  | Sleep | Minutes Asleep | Fitness Watch |
|  | Sleep | Minutes Awake | Fitness Watch |
|  | Sleep | Minutes Light Sleep | Fitness Watch |
|  | Sleep | Minutes Deep Sleep | Fitness Watch |
|  | Sleep | Minutes REM Sleep | Fitness Watch |
|  | Exercise | Activity Calories | Fitness Watch |
|  | Exercise | Marginal Calories | Fitness Watch |
|  | Exercise | BMR Calories | Fitness Watch |
|  | Exercise | Total Calories Burned | Fitness Watch |
|  | Exercise | Continuous Steps (per minute) | Fitness Watch |
|  | Exercise | Fairly Active Minutes | Fitness Watch |
|  | Exercise | Light Active Minutes | Fitness Watch |
|  | Exercise | Very Active Minutes | Fitness Watch |
|  | Exercise | Sedentary Minutes | Fitness Watch |
|  | Exercise | Stress | Fitness Watch |
|  | Patient Information | Age | Patient Interview |
|  | Patient Information | Gender | Patient Interview |
|  | Patient Information | Height | Patient Interview |
|  | Patient Information | BMI | Patient Interview |
|  | Patient Information | Vegetarian | Patient Interview |
|  | Patient Information | Tobacco | Patient Interview |
|  | Patient Information | Alcohol | Patient Interview |
|  | Patient Information | Caffeine | Patient Interview |
|  | Family Information | Father Diabetic? | Patient Interview |
|  | Family Information | Mother Diabetic? | Patient Interview |
|  | Family Information | Sibling Diabetic? | Patient Interview |
|  | Family Information | Grandparents Diabetic? | Patient Interview |
|  | Happiness | Energy | Patient Health Management App |
|  | Happiness | Mood | Patient Health Management App |
|  | Happiness | Cuisine Preferences | Patient Health Management App |
|  | Happiness | Food Ratings | Patient Health Management App |
|  | Happiness | Meal Ratings | Patient Health Management App |
|  | Happiness | Exercise Preferences | Patient Health Management App |
| Symptom Data | Symptom | Headache | Patient Health Management App |
|  | Symptom | Cramps | Patient Health Management App |

TABLE 1-continued

Example Biosignal Data and Source

| Category | Type | Signal | Source |
|---|---|---|---|
|  | Symptom | Numbness | Patient Health Management App |
|  | Symptom | Frequent Urination | Patient Health Management App |
|  | Symptom | Blurred Vision | Patient Health Management App |
|  | Symptom | Tiredness | Patient Health Management App |
|  | Symptom | Excess hunger | Patient Health Management App |
|  | Symptom | Giddiness | Patient Health Management App |
|  | Symptom | Nausea | Patient Health Management App |
|  | Symptom | Vomiting | Patient Health Management App |
|  | Symptom | Diarrhea | Patient Health Management App |
|  | Symptom | Excess thirst | Patient Health Management App |
|  | Symptom | Constipation | Patient Health Management App |
|  | Symptom | Erectile dysfunction | Patient Health Management App |
|  | Symptom | Sleeplessness | Patient Health Management App |
| Medication Data | Medication | Diabetes Medicine | Patient Health Management App |
|  | Medication | Insulin | Patient Health Management App |
|  | Medication | Hypertension Medicines | Patient Health Management App |
|  | Medication | Cholesterol Medicines | Patient Health Management App |
|  | Medication | Obesity Medicines | Patient Health Management App |
|  | Medication | Heart Medicines | Patient Health Management App |
|  | Medication | Arthritis Medicines | Patient Health Management App |
| Nutrition Data | Macronutrients | Net Carb | Nutrition Database/Patient Health Management App |
|  | Macronutrients | Calories consumed | Nutrition Database/Patient Health Management App |
|  | Macronutrients | Net GI Carb | Nutrition Database/Patient Health Management App |
|  | Macronutrients | Fiber | Nutrition Database/Patient Health Management App |
|  | Macronutrients | Fat | Nutrition Database/Patient Health Management App |
|  | Macronutrients | Protein | Nutrition Database/Patient Health Management App |
|  | Macronutrients | Total Carb | Nutrition Database/Patient Health Management App |
|  | Micronutrients | Fructose | Nutrition Database/Patient Health Management App |
|  | Micronutrients | Sodium | Nutrition Database/Patient Health Management App |
|  | Micronutrients | Potassium | Nutrition Database/Patient Health Management App |
|  | Micronutrients | Magnesium | Nutrition Database/Patient Health Management App |
|  | Micronutrients | Calcium | Nutrition Database/Patient Health Management App |
|  | Micronutrients | Chromium | Nutrition Database/Patient Health Management App |
|  | Micronutrients | Omega 3 | Nutrition Database/Patient Health Management App |
|  | Micronutrients | Omega 6 | Nutrition Database/Patient Health Management App |
|  | Micronutrients | ALA | Nutrition Database/Patient Health Management App |
|  | Micronutrients | Q10 | Nutrition Database/Patient Health Management App |

TABLE 1-continued

Example Biosignal Data and Source

| Category | Type | Signal | Source |
|---|---|---|---|
| Micronutrients | Biotin | | Nutrition Database/Patient Health Management App |
| Micronutrients | Flavonoids | | Nutrition Database/Patient Health Management App |
| Glycemic Controllers | Improve IS | | Nutrition Database/Patient Health Management App |
| Glycemic Controllers | Inhibit GNG | | Nutrition Database/Patient Health Management App |
| Glycemic Controllers | Inhibit Carb Absorption | | Nutrition Database/Patient Health Management App |
| Glycemic Controllers | Improve Insulin Secretion | | Nutrition Database/Patient Health Management App |
| Glycemic Controllers | Impr B-Cell Regen | | Nutrition Database/Patient Health Management App |
| Glycemic Controllers | Inhibit Hunger | | Nutrition Database/Patient Health Management App |
| Glycemic Controllers | Inhibit Glucose Kidney Reabsorption | | Nutrition Database/Patient Health Management App |
| Biotanutrients | *Lactococcus* sp. | | Nutrition Database/Patient Health Management App |
| Biotanutrients | *Lactobacillus* sp. | | Nutrition Database/Patient Health Management App |
| Biotanutrients | *Leuconostoc* sp. | | Nutrition Database/Patient Health Management App |
| Biotanutrients | *Streptococcus* sp. | | Nutrition Database/Patient Health Management App |
| Biotanutrients | *Bifidobacterium* sp. | | Nutrition Database/Patient Health Management App |
| Biotanutrients | *Saccharomyces* sp. | | Nutrition Database/Patient Health Management App |
| Biotanutrients | *Bacillus* sp. | | Nutrition Database/Patient Health Management App |
| Glycemic Impact | Glycemic Index | | Nutrition Database/Patient Health Management App |
| Fats | Saturated fat | | Nutrition Database/Patient Health Management App |
| Fats | Mono-unsaturated fat | | Nutrition Database/Patient Health Management App |
| Fats | Polyunsaturated fat | | Nutrition Database/Patient Health Management App |
| Fats | Trans fat | | Nutrition Database/Patient Health Management App |
| Fats | Cholesterol | | Nutrition Database/Patient Health Management App |
| Proteins | Histidine | | Nutrition Database/Patient Health Management App |
| Proteins | Isoleucine | | Nutrition Database/Patient Health Management App |
| Proteins | Lysine | | Nutrition Database/Patient Health Management App |
| Proteins | Methionine + Cysteine | | Nutrition Database/Patient Health Management App |
| Proteins | Phenylalanine + Tyrosine | | Nutrition Database/Patient Health Management App |
| Proteins | Tryptophan | | Nutrition Database/Patient Health Management App |
| Proteins | Threonine | | Nutrition Database/Patient Health Management App |
| Proteins | Valine | | Nutrition Database/Patient Health Management App |
| Vitamins/ Minerals | Vitamin A | | Nutrition Database/Patient Health Management App |
| Vitamins/ Minerals | Vitamin C | | Nutrition Database/Patient Health Management App |
| Vitamins/ Minerals | Vitamin D | | Nutrition Database/Patient Health Management App |
| Vitamins/ Minerals | Vitamin E | | Nutrition Database/Patient Health Management App |
| Vitamins/ Minerals | Vitamin K | | Nutrition Database/Patient Health Management App |
| Vitamins/ Minerals | B1 | | Nutrition Database/Patient Health Management App |
| Vitamins/ | B12 | | Nutrition Database/Patient |

TABLE 1-continued

Example Biosignal Data and Source

| Category | Type | Signal | Source |
|---|---|---|---|
| | Minerals | | Health Management App |
| | Vitamins/ Minerals | B2 | Nutrition Database/Patient Health Management App |
| | Vitamins/ Minerals | B3 | Nutrition Database/Patient Health Management App |
| | Vitamins/ Minerals | B5 | Nutrition Database/Patient Health Management App |
| | Vitamins/ Minerals | B6 | Nutrition Database/Patient Health Management App |
| | Vitamins/ Minerals | Folate | Nutrition Database/Patient Health Management App |
| | Vitamins/ Minerals | Copper | Nutrition Database/Patient Health Management App |
| | Vitamins/ Minerals | Iron | Nutrition Database/Patient Health Management App |
| | Vitamins/ Minerals | Zinc | Nutrition Database/Patient Health Management App |
| | Vitamins/ Minerals | Manganese | Nutrition Database/Patient Health Management App |
| | Vitamins/ Minerals | Phosphorus | Nutrition Database/Patient Health Management App |
| | Vitamins/ Minerals | Selenium | Nutrition Database/Patient Health Management App |
| | Vitamins/ Minerals | Omega 6/omega 3 | Nutrition Database/Patient Health Management App |
| | Vitamins/ Minerals | Zinc/Copper | Nutrition Database/Patient Health Management App |
| | Vitamins/ Minerals | Potassium/ Sodium | Nutrition Database/Patient Health Management App |
| | Vitamins/ Minerals | Calcium/ Magnesium | Nutrition Database/Patient Health Management App |
| | Vitamins/ Minerals | PRAL Alkalinity | Nutrition Database/Patient Health Management App |
| | Metabolic Improvers | Improve BP | Nutrition Database/Patient Health Management App |
| | Metabolic Improvers | Improve Cholesterol | Nutrition Database/Patient Health Management App |
| | Metabolic Improvers | Reduce Weight | Nutrition Database/Patient Health Management App |
| | Metabolic Improvers | Improve Renal function | Nutrition Database/Patient Health Management App |
| | Metabolic Improvers | Improve Liver function | Nutrition Database/Patient Health Management App |
| | Metabolic Improvers | Improve Thyroid function | Nutrition Database/Patient Health Management App |
| | Metabolic Improvers | Improve Arthritis | Nutrition Database/Patient Health Management App |
| | Metabolic Improvers | Reduce uric acid | Nutrition Database/Patient Health Management App |
| | Food Type | Fruits | Nutrition Database/Patient Health Management App |
| | Food Type | Oils | Nutrition Database/Patient Health Management App |
| | Food Type | Spices | Nutrition Database/Patient Health Management App |
| | Food Type | Grains | Nutrition Database/Patient Health Management App |
| | Food Type | Legumes | Nutrition Database/Patient Health Management App |
| | Food Type | Nuts | Nutrition Database/Patient Health Management App |
| | Food Type | Seed Products | Nutrition Database/Patient Health Management App |
| | Cellular Stressors | Inflammatory index | Nutrition Database/Patient Health Management App |
| | Cellular Stressors | Oxidative stress index | Nutrition Database/Patient Health Management App |
| | Cellular Stressors | Gluten | Nutrition Database/Patient Health Management App |
| | Cellular Stressors | Lactose | Nutrition Database/Patient Health Management App |
| | Cellular Stressors | Alcohol | Nutrition Database/Patient Health Management App |
| | Cellular | Allergic index | Nutrition Database/Patient |

TABLE 1-continued

| | Example Biosignal Data and Source | | |
|---|---|---|---|
| Cate-gory | Type | Signal | Source |
| | Stressors | | Health Management App |
| | Hydration | Water | Nutrition Database/Patient Health Management App |

IV. Patient Health Management Platform

IV.A General System Architecture

Figure 3:
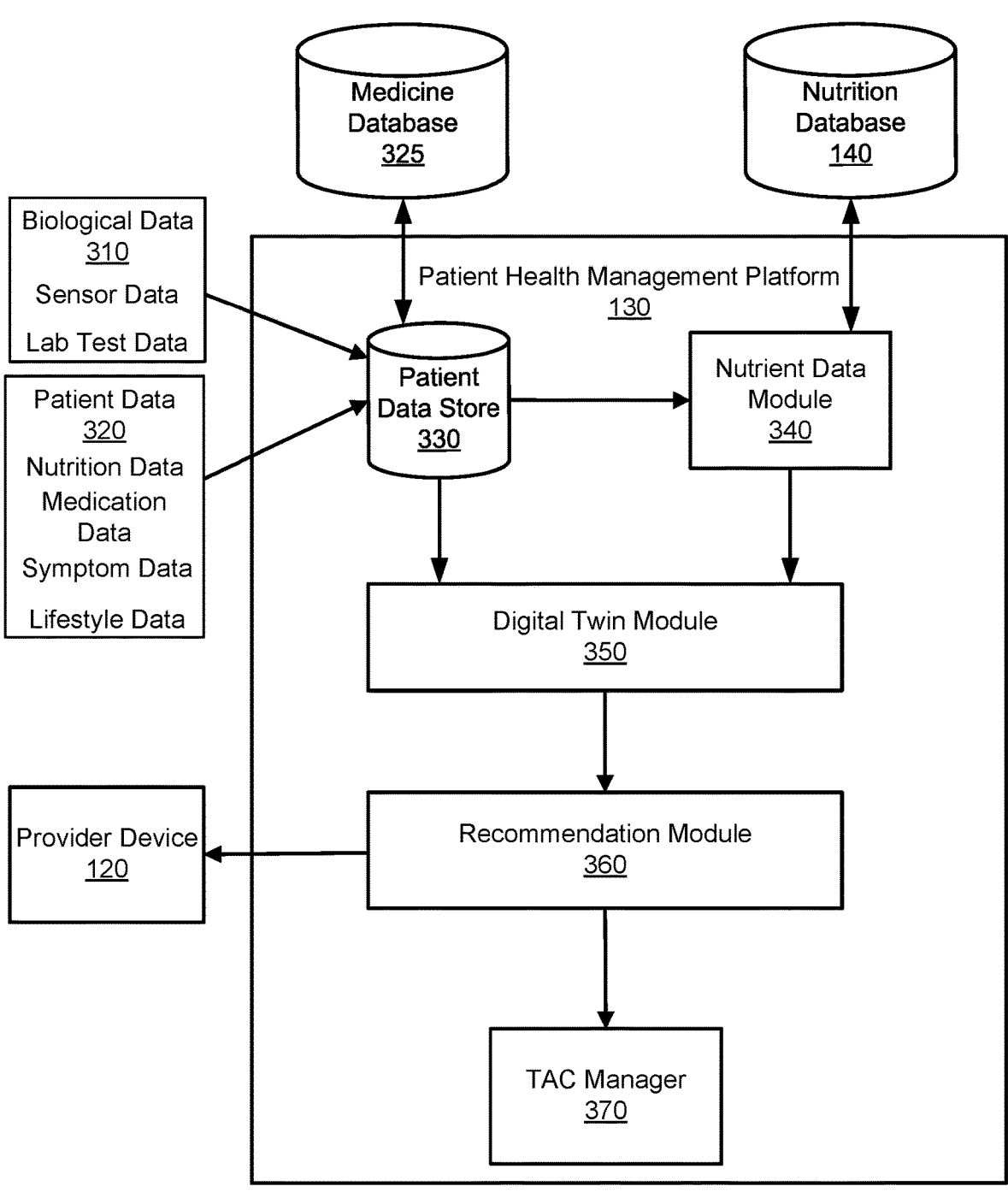
FIG. 3 is a block diagram of the system architecture of a patient health management platform, according to one embodiment.

FIG. 3 is a block diagram of the system architecture of the patient health management platform 130, according to one embodiment. The patient health management platform 130 includes a patient data store 330, a nutrient data module 340, a digital twin module 350, a recommendation module 360, and a TAC manager 370. However, in other embodiments, the patient health management platform 130 may include different and/or additional components.

The patient health management platform 130 receives biological data 310 recorded by a variety of technical sources. Biological data 310 includes sensor data comprising biosignals recorded by one or more sensors worn or implemented by a patient. Such biosignals are continuously recorded and each recorded biosignal is assigned a time-stamp indicating when it was recorded. Biological data 310 further includes lab test data determined based on blood draw analysis and/or other examinations that a patient has been subjected. Biosignals collected through lab test data may be recorded less frequently than biosignals collected through sensor data, for example over bi-weekly or monthly intervals. In some implementations, lab test data is determined based on procedures and analysis performed manually be doctors or researchers or based on analysis performed by machines and computers separate from the metabolic health manager 1000. The patient data store 330 stores biological data 310.

The patient health management platform 130 also receives patient data 320 that is recorded manually by a patient via an application interface on a patient device 110. Patient data 320 includes nutrition data (e.g., nutrition data 320), medication data (e.g., medication data 325), symptom data (e.g., symptom data 330), and lifestyle data. Nutrition data describes a record of foods that a patient has consumed. In some implementations, nutrition data also includes a timestamp indicating when each food was consumed by the patient and a quantity in which each food was consumed. Similarly, medication data describes a record of medications that a patient has taken and, optionally, a timestamp indicating when a patient took each medication and a quantity in which each medication was taken. In response to a patient recording medication data, the patient health management platform may access additional information from a medication database (not shown) to supplement the medication data recorded by the patient. Symptom data describes a record of symptoms experienced by a patient and a timestamp indicating when each symptom was experienced. Lifestyle data describes a record of a patient's physical activity (e.g., exercise) and a record of a patient's sleep history. Lifestyle data may also include a description or selection of emotions or feelings capturing the patient's current state of mind and body (i.e., tired, sore, energetic). In one implementation, each type of patient data 320 may be recorded instantaneously throughout the day when the patient consumes a food, takes a medication, experiences a symptom, or experiences a change in an aspect of their lifestyle. In an alternate implementation, at the end of a day, the patient health management platform 130 detects that a patient has not instantaneously recorded patient data throughout the day and prompts the patient to input a complete record of patient data for the entire day at that time. In addition to biological data 310, the patient data store 330 stores patient data 320.

In some embodiments, the patient data store 330 stores biological data 310 and patient data 330 as an ongoing recorded timeline of entries for a current time period. As new patient data or biological data is recorded or as updates to existing patient data and biological data are received, the patient data store 330 updates the timeline of entries to reflect the new or updated data. Accordingly, the timeline of entries stored in the patient data store 330 comprises foods consumed by the patient at recorded times over the current time period, medications taken by the patient at recorded times over the current time period, and symptoms experienced by the patient at recorded times over the current time period. Some patient data entries may be recorded and reflected in the timeline on a daily basis, whereas other entries are recorded by a patient multiple times a day. Entries for biological data 310, for example, lab test data may be recorded even less frequently, for example as weekly updates to the ongoing timeline. The range of time between a start time and an end time for the current time period may be adjusted manually or trained over time based on predicted and true metabolic states for a patient.

The nutrient data module 340 receives nutrition data from the patient data store 330 and communicates the nutrition data to the nutrition database 140. As described above with reference to FIG. 1, the nutrition database 140 includes comprehensive nutrition information comprising macronutrient information (e.g., protein, fat, carbohydrates), micronutrient information (e.g., Vitamin A, Vitamin B, Vitamin C, sodium, magnesium), and biota nutrients (e.g. *lactococcus, lactobacillus*) for a wide variety of foods and ingredients. In some implementations, the nutrient data module 340 stores nutrition information in a lookup table or combination of lookup tables organized by food item or a category of food item. In other implementations, the nutrient data module 340 stores nutrition information in a lookup table organized by nutrient information or another suitable system. Based on the nutrition data received from the patient data store 330, the nutrient data module 340 identifies nutrition information associated with each food item of the nutrition data and supplements the nutrition data in the patient data store 330 with the identified nutrition information from the nutrition database 140. In some implementations, the nutrient database 140 includes over 100 food-related attributes including, but not limited to, different types of fat, protein, vitamins, and minerals.

The digital twin module 350 generates a digital replica of the patient's metabolic health based on a combination of biological data 310 and patient data 320, hereafter referred to as a digital twin. The digital twin module 350 considers different aspects of a patient's health and well-being to generate and continuously update a patient's digital twin. As described herein, a digital twin is a dynamic digital representation of the metabolic function of a patient's human body. The digital twin module 350 continuously monitors biological data and patient data and correlates a patient's metabolic history with their ongoing medical history to identify changes in the patient's metabolic state. In one embodiment, the digital twin module implements two sets of trained machine-learned metabolic models: a first set of models trained to predict the patient's metabolic state given patient data as inputs and a second set of models trained to determine the patient's true metabolic state given biological data as inputs.

Based on nutrition data, medication data, symptom data, lifestyle data, and supplemental nutrition information retrieved by the nutrient data module 340, the digital twin module 350 generates a prediction of the patient's metabolic state (herein referred to as a patient's "predicted metabolic state"). The digital twin module 350 implements one or more machine-learned, metabolic models to analyze the patient data 320 recorded over a given time period to generate a prediction of the patient's metabolic state for that time period. Accordingly, the prediction of the patient's metabolic state is a function of a large number of metabolic factors recorded in the patient data 320 (e.g., fasting blood glucose, sleep, and exercise) and a nutrition profile (e.g., macronutrients, micronutrients, biota nutrients).

In addition to the predicted metabolic state, the digital twin module 350 may implement one or more metabolic models to generate a true representation of a patient's metabolic state (herein referred to as a "true metabolic state") based on the biological data 310 recorded for a time period. In comparison to the metabolic models used to generate a prediction of a patient's metabolic model, the metabolic models implemented by the digital twin module 350 to determine the true metabolic state of the patient are trained to process aspects of biological data 310 (e.g., wearable sensor data and lab test data) into an affect the patient's metabolic state. For such implementations, at the conclusion of a time period, a metabolic model may be trained to analyze biological data 310 recorded by wearable sensors during the time period and determined based on lab tests from the time period to determine a true metabolic state for the patient that reflects the actual biological conditions experienced by a patient (e.g., their HbA1c levels, or BMI) during the time period. Accordingly, given biological data 310 as an input, the metabolic model is further trained to output a patient's actual biological response (e.g., a measured insulin sensitivity or change in glucose in response to consuming a food or taking a medication).

In some embodiments, digital twin module 350 communicates both the predicted metabolic state and the true metabolic state to the timeliness, accuracy, and completeness (TAC) manager 370. The TAC manager 370 compares the predicted metabolic state and the true metabolic state to determine whether the two states are within a threshold level of similarity to each other. If the two states are within a threshold level of similarity, the manager 370 confirms the timeliness, accuracy, and completeness of the recorded patient data. As described herein, accurately recorded nutrition data, medication data, symptom data, and lifestyle data is accurate in what was recorded in the entry and when the entry was recorded.

Alternatively, if the two states are not within a threshold level of similarity, the TAC manager 370 detects that there is an error in the record of the patient data 320. Examples of such errors detected by the TAC manager 370 include, but are not limited to, an entry recorded in an incorrect amount, a failure to record an entry, or an entry recorded at the wrong time. Based on the inconsistency, or inconsistencies, between the true metabolic state and the predicted metabolic state, the TAC manager 370 identifies one or more potential errors in the recorded patient data which may have contributed to the one or more inconsistencies and generates notifications to the patient device 110 for presentation to the patient.

Patient data and biological data may be recorded at varying intervals. For example, sensor data is recorded continuously every 15 minutes, lab test data is recorded bi-weekly, and patient data 320 is recorded multiple times a day as needed. Therefore, the patient health management platform 130 may not receive an updated recording for every type of data in time to generate a predicted metabolic state. When generating a predicted metabolic state for a particular time period, the digital twin module 350 retrieves all patient data 320 recorded within that time period and the metabolic state predicted by the during the preceding time period. In some embodiments, the digital twin module 350 implements one or more machine learning models to process, as inputs, the recorded patient data and the most recently predicted metabolic state into a predicted metabolic state for a current time period. In place of the most recent predicted metabolic state, the digital twin module 350 may input the most recent true metabolic state to the one or more machine learning models. Accordingly, the predicted metabolic state reflects any effects that the most recently recorded patient data 320 had on a previous metabolic state.

Similarly, when generating a true metabolic state for a time period, the digital twin module 350 retrieves all biological data 310 recorded within that time period (e.g., heart rate, exercise, continuous blood glucose, ketones, blood pressure, weight) and the true metabolic state generated during the preceding time period. The digital twin module 350 may also rely on one or more machine learning models to process the retrieved biological data 310 and the most recent true metabolic state into a current true metabolic state. Accordingly, the generated true metabolic state also reflects any effects of the most recently recorded biological data 310 had on a previous metabolic state. For example, a machine learned model may use a continuous blood glucose signal measured every 15 minutes to calculate a patient's 5-day average blood glucose. The computed measurement is compared against established ranges in the medical literature to determine whether the patients are in a diabetic, pre-diabetic, or non-diabetic state as they progress with their treatment. In common implementations, the digital twin module 350 updates a patient's metabolic state at a higher frequency than a frequency at which lab test data is recorded. As such, when lab test data is unavailable for the current time period, the digital twin module 350 may generate the updated metabolic state based on the lab test data recorded most recently for a preceding time period.

In one embodiment, the recommendation module 360 compares a patient's predicted metabolic state to baseline metabolic state for a patient with a functional metabolism. For patients who already have a functional metabolism, the recommendation module 360 compares the predicted metabolic state to a baseline metabolic state for a patient with an optimal metabolism. In either implementation, the recommendation module 360 determines discrepancies between the patient-specific predicted metabolic state and the baseline metabolic state and identifies one or more biosignals which could be adjusted such that the predicted state becomes more similar to the baseline state, for example lower blood glucose levels in the predicted metabolic state or an imbalance between certain micronutrients and micronutrients.

Based on the determined adjustments, the recommendation module 360 generates a recommendation for improving the patient's biosignals to more closely resemble those of the baseline metabolic state. The recommendation includes a set of objectives for a patient to complete to improve the patient's metabolic health. The set of objectives include a medication regimen or schedule, a food or meal schedule, micronutrient and biota nutrient supplements, one or more lifestyle adjustments, or a combination thereof. The medication regimen, food schedule, and supplement schedule may prescribe medications, food items, or supplements which may either replenish nutrients in which a patient is deficient, offset the effects of nutrients for which a patient has an excess, or a combination thereof. The medication regimen, food schedule, and supplement schedule may also alleviate or mitigate the symptoms (as indicated by symptom data recorded by a patient) that a patient is experiencing by addressing the biological root cause of the symptoms. One example of a medication regimen may include a recommended medication or combination of medications and an adherence schedule for each medication. One example of a food schedule may include a recommended food item or, more broadly, a category of food item and an amount of the food item to be consumed. Similarly, a lifestyle adjustment may prescribe particular lifestyle adjustments for addressing a patient's symptoms or nutrient abnormalities. Examples of lifestyle adjustments include, but are not limited to, increasing physical activity or increasing a patient's amount of sleep. In some implementations, the content of lifestyle adjustments may broadly overlap with food or medication adjustments. For example, a lifestyle adjustment may recommend a patient replace refined carbohydrates with wholegrain foods, while the food schedule includes a set of particular wholegrain foods.

Figure 4:
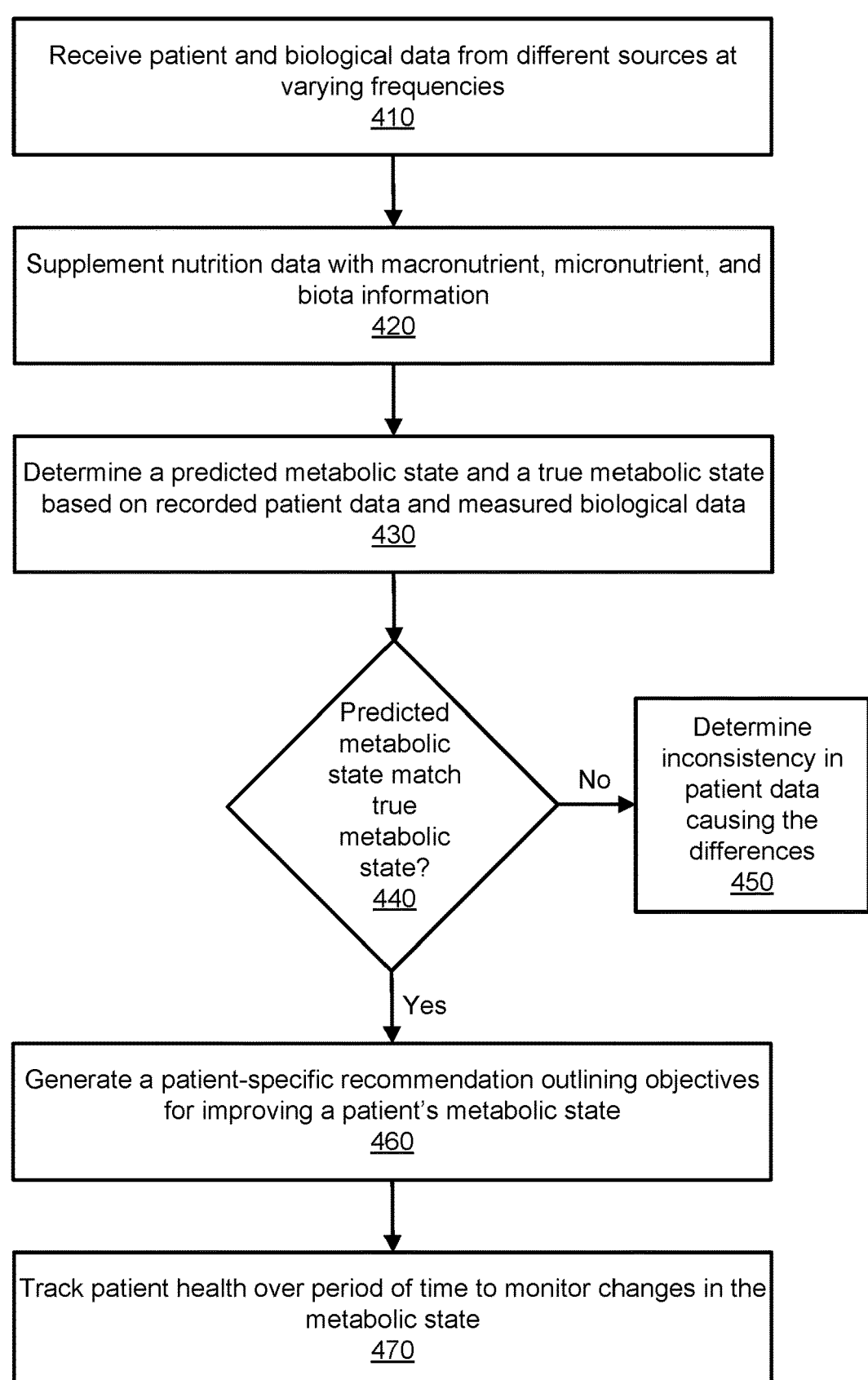
FIG. 4 is a flowchart illustrating a process for generating a patient-specific recommendation for improving metabolic health of a patient, according to one embodiment.

FIG. 4 is a flowchart illustrating a process for generating a patient-specific recommendation for improving metabolic health of a patient, according to one embodiment. The patient health management platform 130 receives 410 patient data and biological data from different sources at varying frequencies. Patient data describes data manually recorded by a patient and communicated to the platform 130. Biological data describes data manually recorded by wearable sensors or measured based on lab tests before being communicated to the platform 130.

Patient data includes nutrient data which is recorded by the patients as a list of foods which have been consumed by the patient over a time period. While the impact of a food item by itself on a patient's metabolic state may not be known, the impact of particular macronutrients, micronutrients, and biota nutrients associated with the food item on a patient's metabolic state is known. As a result, the patient health management platform 130 accesses a nutrition database 140 storing such macronutrient, micronutrient, and biota nutrient information. Based on the accessed information, the platform 130 supplements 420 the recorded nutrition data with the accessed macronutrient, micronutrient, and biota information.

Consistent with the description above in Section IV.A, the platform 130 determines 430 a predicted metabolic state based on the recorded patient data (e.g., patient data 320) and the patient's true metabolic state based on the measured biological data (e.g., biological data 310). The platform 130 compares 440 the predicted metabolic state with the true metabolic state to determine whether the two states match or are within a threshold level of similarity. If the two metabolic states are not within the threshold level of similarity, the platform 130 determines 450 one or more inconsistencies in the patient's recording of their patient data, which may have caused the predicted metabolic state to differ from the true metabolic state. The platform 130 communicates the inconsistency back to a patient device (i.e., patient device 110). Upon receiving the inconsistency, the patient device 110 presents a user interface notifying the patient of the inconsistency and enabling the patient to correct the inconsistency. The platform 130 receives the updated patient data and determines 430 an updated predicted metabolic state based on the updated patient data.

If the two metabolic states are within a threshold level of similarity, the platform 130 categorizes the predicted metabolic state as representative of poor metabolic health, functional metabolic health, or optimal metabolic health. Based on the assigned category, the platform 130 generates 460 a patient-specific recommendation outlining objectives for improving the patient's metabolic state. In particular, the recommendation may outline objectives for consuming food, taking medication, or engaging in lifestyle adjustments to supplement nutrients in which a patient is deficient and that may have contributed to the patient's deteriorated metabolic state.

Following the receipt of the recommendation, a patient continues to record patient data and wearable sensors continue to record biological data, both of which are representative of a metabolic state for a subsequent time period. As patient data and biological data continue to be recorded, the patient health management platform 130 tracks 470 patient health over a time period to monitor changes in the patient's metabolic state. Based on the monitored changes, the platform 130 is able to confirm whether or not a patient is adhering to the recommendation generated by the platform 130. If the patient is not adhering to the recommendation, the platform 130 may generate a notification or reminder to the patient, a doctor assigned to the patient, a coach assigned to the patient, or a combination thereof. If that patient adheres to the recommendation, the platform 130 is able to review the changes in metabolism to confirm that the recommendation is improving the patient's metabolic health. If the platform is not improving the patient's metabolic health, the platform 130 is able to dynamically revise the recommendation to correct the deficiencies of the initial recommendation. If the platform is improving the patient's metabolic health, the platform 130 is able to dynamically update the recommendation to continue to optimize the patient's metabolic health in view of their improved metabolic state.

More information regarding the patient health management platform 130 and its components, as well as the interactions between those components, can be found in U.S. patent application Ser. No. 16/993,177, filed Aug. 13, 2020, U.S. patent application Ser. No. 16/992,184, filed Aug. 13, 2020, and U.S. patent application Ser. No. 16/993,189, filed Aug. 13, 2020, each of which are incorporated by reference herein in their entirety.

IV.C Metabolic Digital Twin

Figure 5:
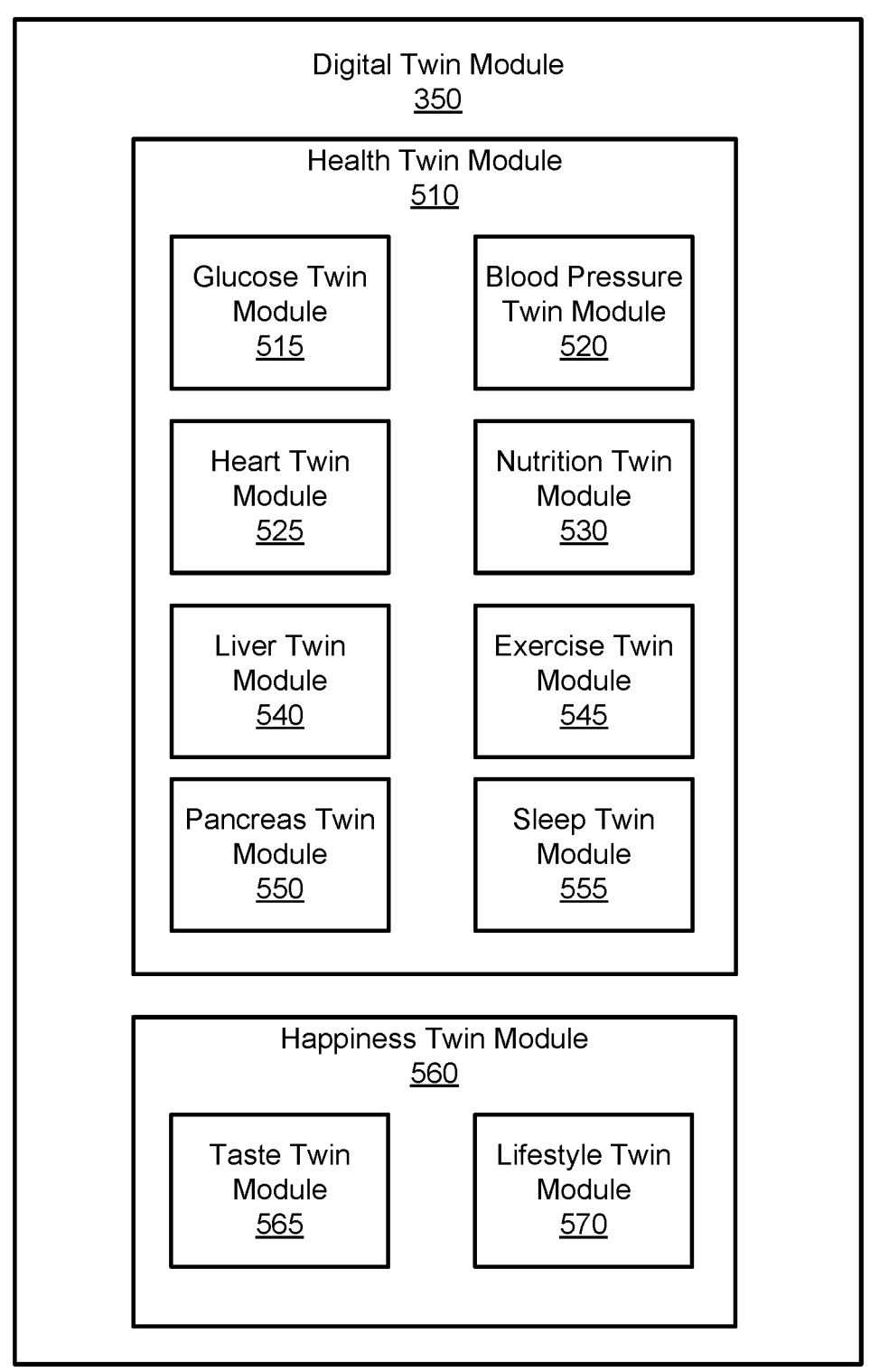
FIG. 5 is a block diagram of the system architecture of a digital twin module, according to one embodiment.

As described above, the digital twin module 350 generates a digital twin of the patient's metabolic health to continuously monitor and update different aspects of a patient's health and well-being. FIG. 5 is a block diagram of the system architecture of a digital twin module 350, according to one embodiment. The digital twin module 350 includes a health twin module 510 and a happiness twin module 560. The digital twin module 350 may include different and/or additional components to perform the same functions described with regards to the digital twin module 350. The digital twin module 350 generates a digital replica of a patient's metabolic state in two dimensions: a health dimension and a happiness dimension.

The health twin module 510 generates a digital replica of the health dimension of a metabolic state based on biological measurements recorded by wearable sensors and lab test data. In the embodiment illustrated in FIG. 5, the health twin module 510 comprises a glucose twin module 515, a blood pressure twin module 520, a heart twin module 525, a nutrition twin module 530, a liver twin module 540, an exercise twin module 545, a pancreas twin module 550, and a sleep twin module 555. Each component of the health twin module 510 captures and updates a critical aspect of a patient's metabolic health such that the digital twin represents the patient's overall metabolic health. The health twin module 510 may include additional, fewer, or a different combination of components to generate a digital twin based on varying aspects of a patient's metabolic health. In some embodiments, each component of the health twin module 510 generates an output indicating a condition of an aspect of the patient's metabolic health. For example, the heart twin module 525 may generate an output indicating the patient's heart health rating on a scale of 100, for example 85. This is derived from cardiac health biomarkers such as Lipoprotein (a), Apolipoprotein B, and High-Sensitivity C-Reactive Protein (HS-CRP).

The glucose twin module 515 tracks and analyzes glucose dynamics for a patient over time to enable the digital twin to model glucose dynamics for the patient. The glucose twin module 515 may analyze glucose dynamics recorded via a wearable sensor. The heart twin module 525, liver twin module 540, and the pancreas twin module 550 track and analyze function and physiology of a patient's heart, liver, and pancreas to enable the digital twin to model heart, liver, and pancreas function for the patient. The heart twin module 525, the liver twin module 540, and the pancreas twin module 550 may analyze function of a patient's heart, liver, and pancreas based on information recorded via one or more lab tests. The blood pressure twin module 520 tracks and analyzes blood pressure dynamics for a patient over time to enable the digital twin to model blood pressure dynamics for the patient. The blood pressure twin module 520 may analyze blood pressure dynamics recorded via a wearable sensor or via lab test data. The glucose twin module 515 is further described with reference to FIGS. 8A-C.

The nutrition twin module 530 communicates with the nutrient data module 530 to track and analyze nutrition information of food consumed by a patient to enable the digital twin to model the impact of food consumed by the patient. The nutrition twin module 530 may analyze a combination of macronutrient parameters, micronutrient parameters, and biota nutrients for each food item recorded by the patient through a patient device 110. The exercise twin module 545 tracks exercise activity for a patient and analyzes those exercise habits by correlating periods of exercise (or inactivity) with changes in the patient's metabolic state. The exercise twin module 545 may analyze exercise activity recorded by the patient through a patient device 110. Similarly, the sleep twin module 555 tracks sleep trends for a patient and analyzes those sleep trends by correlating quality, length, and frequency of sleep with changes in the patient's metabolic state. The sleep twin module 555 may analyze sleep trends recorded by the patient through a patient device 110 or by a wearable sensor.

Each module (or component) of the health twin module 510 is connected to and communicates with other modules of the health twin module 510 to capture the complex interaction effects that contribute to a patient's metabolic state. For example, blood pressure dynamics are driven by a combination of factors including blood glucose dynamics, heart function, nutrition, exercise, and sleep trends. Each of those driving factors are, in turn, driven by other factors represented in the patient's digital twin.

The happiness twin module 560 generates a digital replica of the happiness dimension of a patient's metabolic state based on feedback recorded through a patient device 110. In the embodiment illustrated in FIG. 5, the happiness twin module 560 comprises a taste twin module 565 and a lifestyle twin module 570. Each component of the happiness twin module 560 captures a critical aspect of a patient's satisfaction with their recommended treatment to their digital twin such that the digital twin also represents the patient's overall experience with treatment. The happiness twin module 520 may include additional, fewer, or a different combination of components to generate a digital twin based on varying aspects of a patient's metabolic health. In some embodiments, each of the taste twin module 565 and the lifestyle twin module 565 generate an output indicating a patient's current state of mind regarding a food item, meal recommendation, or a lifestyle recommendation prescribed by a patient-specific recommendation. For example, each food consumed by a patient may be labeled with a score on a 5-star scale, such as "4 stars".

The taste twin module 565 communicates with the nutrition twin module 530 to assign a preference to each food item recorded by the patient (e.g., a label indicating whether the patient enjoyed the food item or not). In conjunction, the nutrition twin module 530 and the taste twin module 565 may compare two foods with a similar metabolic effect and prioritize whichever food the patient enjoyed more. The food item that the patient enjoyed more will be carried forward in other future patient-specific recommendations. The lifestyle twin module 570 communicates with the exercise twin module 545 and the sleep twin module 555 to assign a preference to the activities recorded by the patient. For example, if a patient wishes to engage in more exercise, future treatment recommendations may be generated with an emphasis on more frequent exercise.

As described herein, each module of the health twin module 510 and the happiness twin module 560 includes a uniquely trained metabolic model. In particular, when generating a prediction of a patient's metabolic state, each involved metabolic model is trained to determine an impact of a particular type of patient data input on a patient's metabolic state. When generating a prediction of a patient's metabolic state, the digital twin module 350 may consider the output of the metabolic models trained to receive patient data as inputs, for example the nutrition twin module 530, the exercise twin module 545, the sleep twin module 555, and the lifestyle twin module 570. For example, the nutrition twin module 530 implements a metabolic model to predict a patient's metabolic state based on patient data identifying food items consumed by the patient. As additional examples, each of exercise twin module 545, the sleep twin module 555, and the lifestyle twin module 570 implement a metabolic model to predict a patient's metabolic state based on patient data describing the patient's exercise habits, sleep habits, and lifestyle habits, respectively. The digital twin module 350 may also consider metabolic models that are not illustrated in FIG. 5, or the other twin modules that are illustrated in FIG. 5 when generating a prediction of a patient's metabolic state.

In comparison, each metabolic model involved in determining a patient's true metabolic state is trained to determine an impact of a particular type of biosignal input on a patient's metabolic state, for example the glucose twin module 515, the blood pressure twin module 520, the heart twin module 525, the liver twin module 540, and the pancreas twin module 550. For example, the glucose twin module 515 implements a metabolic model to evaluate a patient's true metabolic state based on input biosignals describing the glucose dynamics of the patient. As additional examples, each of the heart twin module 525, the liver twin module 540, and the pancreas twin module 550 implement metabolic models to evaluate, respectively, a true performance of a patient's heart, liver, and pancreas based on input biosignals describing the functionality of those organs. As yet another example, the blood pressure twin module 520 implements a metabolic model to evaluate a patient's true metabolic state based on input biosignals describing blood pressure dynamics of the patient. The digital twin module 350 may also consider metabolic models that are not illustrated in FIG. 5, or the other twin modules that are illustrated in FIG. 5 when generating a prediction of a patient's metabolic state.

In some embodiments, modules of the digital twin module 350 may implement a combination of multiple machine-learned models to more accurately and completely characterize each aspect of a patient's metabolic health. For example, as will be described below in Section IV.D, the glucose twin module 515 may implement both a glucose impact model (as described in Section IV.D.1) and a 1-Day Average Glucose model (as described in Section IV.D.2).

After a digital twin of a patient has been initialized, components of the digital twin module 350 continuously collect data describing changes in conditions contributing to the patient's metabolic health. When any component of the digital twin module 350 receives updated data, the digital twin module 350 updates a digital twin of the patient in near real-time to reflect the updated data.

IV.D Machine-Learned Metabolic Models

Because the human body is a complex system and different patients may respond differently to the same input stimuli, the patient health management platform 130 includes mathematical models trained to learn the relationships between response signals representing a patient's metabolic states and input stimuli causing those responses. As described above, the patient health management platform 130 applies machine-learning based artificial intelligence to generate a precision treatment recommendation for improving a patient's metabolic health by predicting their response to future input stimuli. The digital twin module 350 implements a combination of machine-learned models that are trained to predict a response of the human body based on each patient's current metabolic state and a set of inputs (e.g., recorded patient data, sensor data, and biological data). Each machine-learned model enables the digital twin module 350 to automatically analyze a large combination of biosignals recorded for each patient to characterize a patient's current or potential metabolic state.

In order to model a patient's metabolic state and to track changes in their metabolic health, a model, such as a mathematical function or other more complex logical structure, is trained using the combination of input biosignals described above, to determine a set of parameter values that are stored in advance and used as part of the metabolic analysis. Briefly, a representation of a patient's metabolic state is generated by inputting wearable sensor data, lab test, and recorded patient data as input values to the model's function and parameters, and, together with values assigned to those parameters, determines a patient's metabolic health. As described herein, the term "model" refers to the result of the machine learning training process. Specifically, the model describes the generation of a function for representing a patient's metabolic state and the determined parameter values that the function incorporates. "Parameter values" describe the weight that is associated with at least one of the featured input values. "Input values" describe the variables of the function or the conditions to be used in conjunction with the parameter values to determine the risk score. Input values can be thought of as the numerical representations of the various features that the model takes into account, for example the input biosignals. During training, from input values of the training dataset, the parameter values of a model are derived. Further, the training data set is used to define the parameter values at a specified time interval, whereas the input values are continuously updated by the patient's conditions.

The digital twin module 350 may include a combination of machine-learned models to generate various representations of a metabolic state, for example the metabolic models trained to predictively model a patient's metabolic state based on recorded nutrition data, medication data, symptom data and lifestyle data, and to model a patient's true metabolic state based on sensor data and lab test data. The digital twin module 350 may input patient data 320, for example nutrition data, medication data, symptom data, or lifestyle data, into a combination metabolic models (e.g., the nutrition twin model 530 and the lifestyle twin module 570) to predict a patient's metabolic state that would result from the recorded patient data. The digital twin module 350 may compare a recorded timeline of patient data (e.g., foods consumed by the patient, medications taken by the patient, and symptoms experienced by the patient) during a time period to a metabolic state generated for the time period to determine an effect of each food item, medication, and symptom on the metabolic state of the patient.

Additionally, the digital twin module 350 may implement one or more metabolic models to predict a patient's metabolic state that would result from the recommended nutrition, medication, or lifestyle changes included in a recommendation. Alternatively, the digital twin module 350 may receive biological data, for example sensor data and lab test data, as inputs to metabolic models to determine a patient's actual metabolic response to the patient data 320.

Each metabolic model is trained using a training dataset made up of large volumes of historical patient data and biological data recorded for a significant volume of patients, respectively. The training set includes daily metabolic inputs and corresponding daily metabolic outputs. Inputs, for example, include patient data 320 recorded for a current time period (i.e., different foods, medication, sleep, exercise, etc.) and a patient's initial metabolic state before the patient data 320 was recorded (e.g., based on biosignals derived from sensor data and lab test data). Inputs measured by wearable sensors and lab tests or recorded manually by a patient may be encoded into a vector representation, for example a feature vector, that a machine-learned model is configured to receive. A feature vector comprises an array of feature values each of which represents a measured or recorded value of an input biosignal.

Outputs, for example, include the actual biological data 310, which represents biosignals characterizing a patient's metabolic health (i.e., blood glucose level, blood pressure, and cholesterol). These act as baseline models trained on historical data that can then be applied to new patients with metabolic issues needing treatment to make predictions about those new patients based on what the models have learned from historical patients. Once trained, the machine-learned model may be applied to predict new metabolic states for the new patients based on new combinations of biosignals to predict how a novel set of input biosignals would result in different output signals, for example lowering blood glucose to improve diabetes or lowering blood pressure to improve hypertension.

The models are continuously trained by feeding the input biosignals and metabolic state outcomes for existing and new patients into these models such that the models continue to learn and are continuously updated based on these new data points. For example, after a metabolic state model determines an aspect of a patient's true metabolic state for a time period, the digital twin module 350 may update a training dataset with the determined true metabolic state and a plurality of biosignals recorded during the time period that contributed to the true metabolic state. The metabolic state model(s) are periodically re-trained based on the updated training dataset. This continuously improves the model and allows it to accurately predict future metabolic states for each patient based on their biosignal inputs. In comparison, the metabolic state model is trained or re-trained/modified on a training dataset comprising the information described above for a particular patient.

FIG. 6 is an illustration of the process for training a machine-learned model to output an aspect of a patient's metabolic health, according to one embodiment. The digital twin module 350 retrieves 610 a training dataset comprised of historical biosignals (e.g., historical sensor data and lab test data) and patient measured and/or recorded for an entire population of patients. Each historical measurement of biological data and record of patient data is assigned a timestamp representing when the patient experienced the measurement/recording and a label identifying its impact on a patient's metabolic health, the patient's metabolic response to the measurement, or both. Using the training dataset of population-level data, the digital twin module 350 trains 620 a baseline model. The training dataset of population-level data comprises labeled metabolic states recorded for a population of patients and sensor data and lab test data that contributed to each labeled metabolic state. Once trained, the baseline model may be implemented to determine a metabolic state of a representative patient of the population of patients (e.g., an average patient) given a set of biological inputs, for example biological data or patient data.

In some implementations, the baseline model may be further trained to generate a personalized representation of a patient's metabolic health. In such implementations, the digital twin module 350 generates 630 an additional training dataset of biological data and patient data for a particular patient. The digital twin module 350 accesses both measured biological data and recorded patient data for a particular patient and aggregates that data into a training dataset. Similar to the historical training dataset, the biological data and patient data of the training dataset are assigned a timestamp and a label to characterize how each biological input impact the particular patient's metabolic state. Using the training dataset of patient-specific data, the digital twin module 350 trains 640 a personalized metabolic model. Once training, biological data and patient data recorded during a subsequent time period may be input 650 to the trained model to output a representation of a particular patient's metabolic state.

Depending on the type of data input to either the personalized or baseline metabolic model, the digital twin module 350 may generate a representation of a patient's true metabolic state or their predicted metabolic state. Biological data, for example data recorded by a wearable sensor or a lab test, may be input to a model to generate a representation of a patient's true metabolic state consistent with the description above. Alternatively, patient data, for example nutrition data, medication data, symptom data, and lifestyle data, may be input to a model to generate a prediction of patient's current metabolic state consistent with the description above.

Training both models in such a manner enables the patient health management platform 130 to predict a patient's metabolic response to future input stimuli (i.e., patient data 320 recorded by a patient in the future) for not just patients already included in the training dataset, but also new patients included in a holdout dataset because the model only relies on the knowledge representing a patient's current metabolic state and the patient's input stimuli to predict their patient-specific response. Additionally, the model predicts a patient's response to input stimuli for each patient at different stages of his or her treatment because the platform maintains a history of a patient's changing metabolic condition. Finally, it allows for long-range precision prediction of the patient's metabolic state by using current and short-range predictions to inform longer-range predictions.

Figure 7:
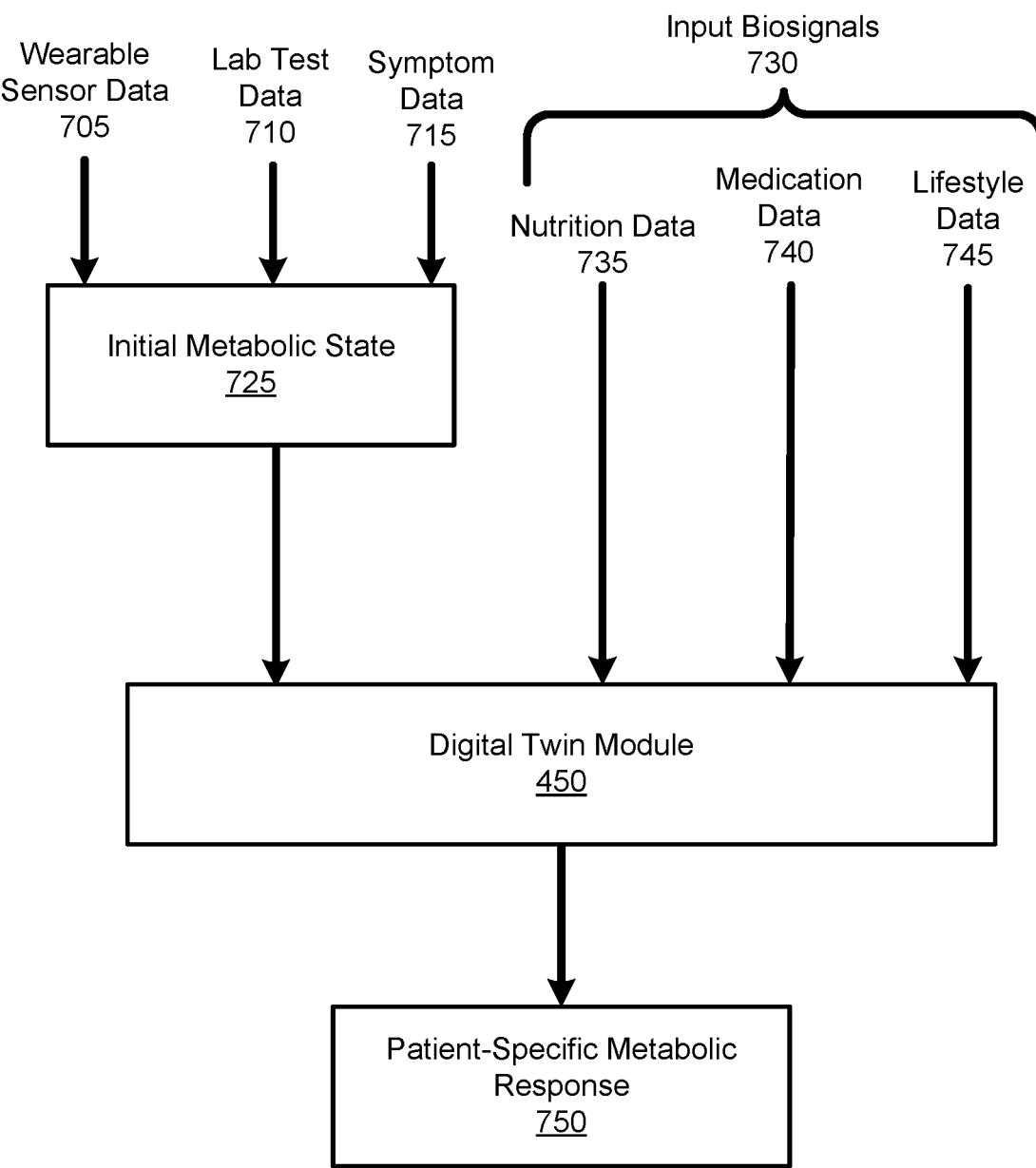
FIG. 7 is an illustration of the process for implementing a machine-learned model to predict a patient-specific metabolic response, according to one embodiment.

FIG. 7 is an illustration of the process for implementing a machine-learned model, according to one embodiment. For a given time period, biosignals recorded as wearable sensor data 705, lab test data 710, and symptom data 715 are representative of a patient's actual, current metabolic state. Accordingly, based on these input biosignals, the patient response module generates an initial metabolic state 725. When sufficient training data exists for a particular patient, the initial metabolic state 725 may be determined using a metabolic model(s). Alternatively, the initial metabolic state 725 may be determined using metabolic model(s) trained for a population of patients. Additionally, the digital twin module 350 relies on input biosignals 730, which represent biosignals that may impact a patient's metabolic state, either deteriorating or improving the state. For example, input biosignals 730 may include nutrition data 735, medication data 740, and lifestyle data 745 recorded for a patient at a time occurring after the generation of the initial metabolic state. In addition to the initial metabolic state 725, the digital twin module 350 receives the input biosignals 730 recorded by the patient as inputs one or more metabolic models. Accordingly, digital twin module 350 models the patient's patient-specific metabolic response 750 to the inputted biosignals. Described differently, the patient-specific metabolic response 750 represents one or more changes in a patient's initial metabolic state caused by, or at least correlated with, the input biosignals 730.

For a second time period following the determination of the patient-specific metabolic response 750, the platform 130 continues to record wearable sensor data 705, lab test data 710, and symptom data 715. Given biosignals recorded as wearable sensor data 705 and lab test data 710 as inputs, the aggregated output of the combination of metabolic models (e.g., the true metabolic state) describes what a patient's metabolic response actually is during a time period. Given nutrition data, 735, medication data 740, and lifestyle data 745 (e.g., input biosignals 730) recorded during the same time period as inputs, the aggregated output of the combination of metabolic models (e.g., the predicted metabolic state) describes what a patient's metabolic response should be during the time period. Accordingly, a comparison of the two outputs allows the platform 130 to verify the timeliness, accuracy, and completeness with which a patient recorded the input biosignals 730.

IV.D.1 Virtual Blood Pressure Monitor

Figure 8A:
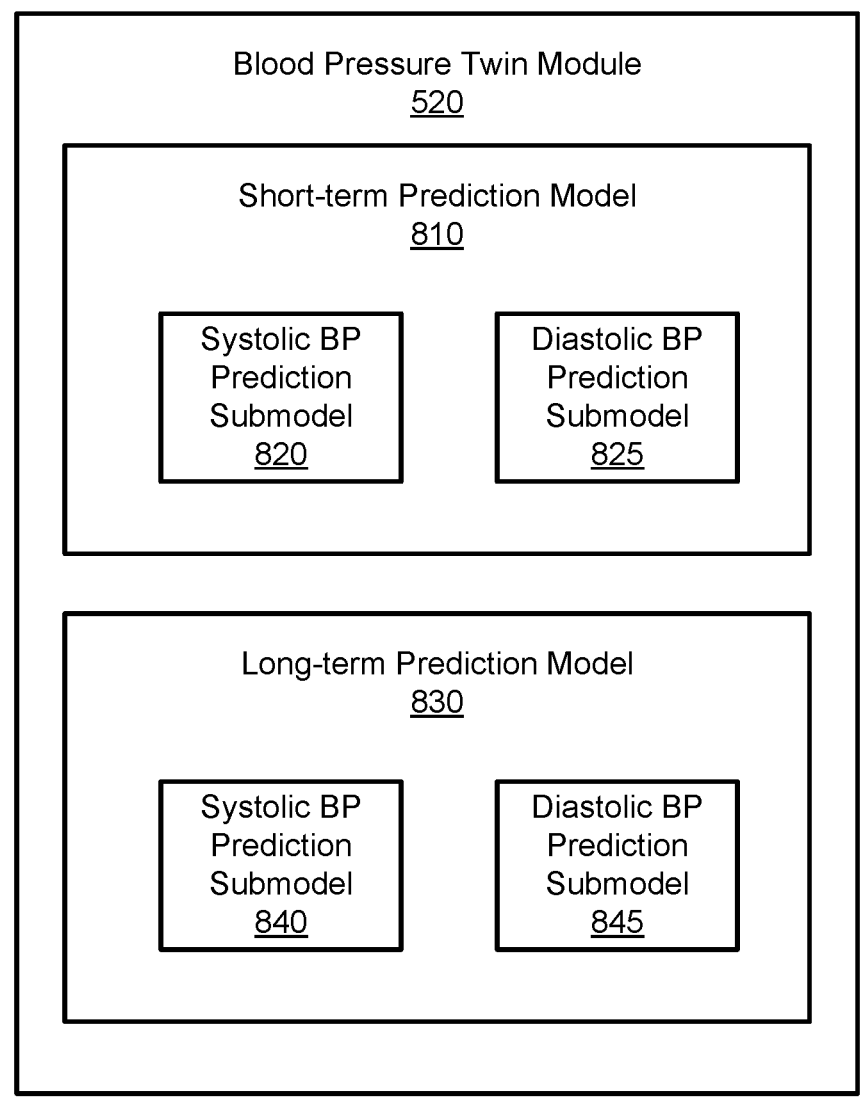
FIG. 8A is a block diagram of the system architecture of a blood pressure twin module 520, according to one embodiment.

The blood pressure twin module 520 implements a combination of machine-learned models to generate predictions of a patient's blood pressure after or during various situations and conditions. FIG. 8A is a block diagram of the system architecture of a blood pressure twin module 520, according to one embodiment. The blood pressure twin module 520 includes a short-term prediction model 810 and a long-term prediction model 830. The blood pressure twin module 520 may include different and/or additional components to perform the same functions described with regards to the blood pressure twin module 520. The short-term prediction model 810 generates regular (e.g., daily) predictions of a patient's systolic and diastolic blood pressures. The long-term prediction model 830 generates regular, accurate predictions of a patient's systolic and diastolic blood pressure levels over longer periods of time, for example weeks, months, or years.

As described above with reference to FIG. 6, both the short-term prediction model 810 and the long-term prediction model 830 apply a training dataset of historical blood pressure data from a population of patients to each machine-learned model to generate a baseline model. As described herein, each baseline model is trained to generate a blood pressure prediction at the population level based on biological data, for example sensor data and lab test data, collected from the population. When a patient initializes a profile on the patient health management platform, the baseline models of one or both of the short-term prediction module 810 and the long-term prediction module 825 are further fine-tuned to the metabolic state of the patient using a patient-specific training dataset including sensor data and lab test data collected from the patient. Accordingly, the patient-specific training dataset is fine-tuned to the metabolic state of the patient to characterize the specific metabolic state and condition of the patient. In some embodiments, the patient-specific training dataset is a compilation of previous true blood pressure measurements for the patient and historical biosignals recorded for the patient that contributed to each previous true blood pressure measurement. As described herein, a patient's true blood pressure is measured using physical blood pressure monitors. Over the course of an initialization period (e.g., a patient's first 35 days using the platform 130), lab test data, sensor data, and patient data are collected for the patient and correlated with the patient's true blood pressure. During the initialization period, a patient may wear a physical DBPM to monitor their true blood pressure, but after the initialization period the patient may stop wearing the physical DBPM. Following the conclusion of the initialization period, sensor data may be recorded by non-invasive sensors worn by the patient, for example a fitness tracker or a fitness watch, configured to monitor their heart rate and to track their physical activity.

Using a combination of trained, patient-specific models, the blood pressure twin module 520 generates accurate estimations of a patient's blood pressure levels based on a combination of sensor data and lab test data recorded for the patient. The blood pressure twin module 520 updates metabolic parameters of a digital twin of the patient's metabolic state (for example, as describe above with reference to FIG. 5) in view of its most recent estimations of the patient's blood pressure.

The trained combination of one or more machine-learned models implemented by the blood pressure twin module 520, which may also be referred to herein as a "virtual BPM", provides a patient with a superior experience compared to conventional MBPM, DBPM, and ABPM technologies. Compared to those conventional technologies, the virtual BPM described herein is more suitable for long-term blood pressure monitoring (e.g., time periods extending for months and years). The virtual BPM (e.g., the blood pressure twin module 520) generates accurate estimations of blood pressure in the long-term using only passively-collected biosignal data, with minimal patient engagement and no specific routine for taking blood pressure readings resulting in improved patient adherence compared to conventional MBPM's, DBPM's, and ABPM's. Additionally, the virtual BPM generates consistently accurate blood pressure predictions without requiring that a patient precisely position the cuff of a conventional MBPM, DBPM, and ABPM follows stringent measurement procedures.

The blood pressure twin module 520 generates predictions of a patient's systolic and diastolic blood pressure levels, for example in millimeters of mercury (mmHg), just as physical BPM's do. In some embodiments, the blood pressure twin module 520 further classifies a patient's predicted blood pressure level based on categories defined by the American Heart Association (e.g., normal, elevated, high blood pressure stage 1, high blood pressure stage 2, and hypertensive crisis). Accordingly, a patient is able to continuously monitor changes in their hypertension conditions based on the predictions generated by the blood pressure twin module 520. As an example, if the blood pressure twin module 520 determines that a patient has elevated blood levels, the patient recommendation module 360 provides daily guidance to the patient with instructions for improving their blood pressure levels or preventing their blood pressure levels form worsening to Stage 1 or Stage 2 hypertension.

The short-term prediction model 810 comprises two sub-models: a systolic BP prediction submodel 820 and a diastolic BP prediction submodel 825. The systolic BP prediction submodel 820 generates a daily prediction of a patient's systolic blood pressure. The diastolic BP prediction submodel 825 generates a daily prediction of a patient's diastolic blood pressure. In one embodiment, the short-term prediction model 810 implements gradient boosting techniques (e.g., gradient boosted decision trees from the CatBoost library trained using the CatBoostRegressor from the CatBoost package) to generate predictions of a patient's systolic and diastolic blood pressure. The short-term prediction model 810 is trained to generate daily blood pressure predictions for a patient base on a combination of biosignal inputs organized into the following categories: sleep data, exercise data, heart rate data, medication data, blood glucose data, and nutrition data. Examples on inputs categorized as sleep data include, but are not limited to, an amount of time a patient spends away (e.g., in minutes), an amount of time the patient spends asleep, an amount of time the patient spends in bed, a timestamp when the patient awoke, and a timestamp when the patient fell asleep. Examples of inputs categorized as heart rate data include, but are not limited to, a mean heart rate, a median heart rate, a $10^{th}$ percentile of the heart rate, and a measure of the heart rate at the time when the blood pressure measurement was taken. Examples of inputs categorized as medication data include, but are not limited to, a number of blood pressure medicines regularly taken by a patient and an aggregate of scores assigned to each blood pressure medicine.

Examples of inputs categorized as blood glucose data include, but are not limited to, an hbA1c value measured during a patient's most recent lab test, an overnight minimum of a 1-hour rolling average of the patient's blood glucose as measured by a CGM, a maximum of a 1-hour rolling average of the patient's blood glucose, a daily average over five days of the standard deviation of the patient's blood glucose measurements, a single day average of the patient's blood glucose measurements, and a measurement representing the amount of insulin resistance a patient displays (e.g., Homeostatic Model Assessment for Insulin Resistance).

Examples of inputs categorized as nutrition data include, but are not limited to, measurements of lactose, gluten, selenium, phosphorous, manganese, zinc, copper, folate, vitamin B6, vitamin B5, vitamin B3, vitamin B2, vitamin B1, vitamin K, vitamin E, vitamin D, vitamin C, vitamin A, cholesterol, trans fat, polyunsaturated fat, monounsaturated fat, saturated fat, fructose, flavonoids, biotin, q10, alphaliphoic acid, omega 6, omega 3, chromium, calcium, magnesium, potassium, sodium, and caffeine. Additional examples include levels of amino acids eaten in foods, valine, threonine, tryptophan, phenylalanine and tyrosine, methionine and cysteine, lysine, isoleucine, and histidine. Nutrition data may additionally include measurements of live bacterial intakes, for example intake of *bacillus, saccharomyces, Bifidobacterium, streptococcus, leuconostoc, lactobacillus,* and *Lactococcus*. Nutrition data may additionally include macronutrient consumption, for example calories, carbs, proteins, fats, and fibers.

The long-term prediction model 830 generates accurate estimations of a patient's blood pressure over an extended time period. More specifically, the long-term prediction model 830 is time-independent and capable of accurately estimating blood pressure levels for many months after a patient's last physical BPM reading. The long-term prediction model 830 comprises two submodels: a systolic BP prediction submodel 840 and a diastolic BP prediction submodel 845. The systolic BP prediction submodel 840 generates a long-term prediction of a patient's systolic blood pressure and the diastolic BP prediction submodel 845 generate a long-term prediction of a patient's diastolic blood pressure.

Each of the submodels 840 and 845 are trained to analyze two sets of inputs: sequential features and static features. Sequential features represent passively recorded sensor data that continuously changes over time including per-minute heart rate and step counts, patient medication information, and time-based interaction features (e.g., elapsed time between consecutive inputs, elapsed time between inputs and labels, etc.). Static features refer to biological data measured or calculated at a single point in time including patient medication information, results of lab tests, and features derived from those lab tests. Static features measured or calculated based on the most recent lab test are carried forward for each day leading up to the patient's next lab test or set of lab tests. Examples of static features measured in lab tests include, but are not limited to, "ast", "redBloodCells", "hemoglobin", "glucose", "insulin", "protein", "urea", "potassium", "creatinine", "sodium", "chloride", "calcium", "veinHbalc", and "ketoacidosis". Each of the above static features of lab test data are described above with reference to Table 1. Examples of static features derived from lab test data include, but are not limited to, "homaIR", "measured_homaIR", "tghdlratio", "tgglucindex", "measured_tghdlratio", "measured_tgglucindex", "glucscore", "ketscore", "glucose_ketone_index", "cpepcgm", "hgp_score". Each of the derived static features are further described below.

The derived feature "homaIR" represents the Homeostatic Model Assessment for Insulin Resistance, which is a measurement of the amount of insulin resistance a patient exhibits. The feature "homaIR" may be calculated based on lab test data derived from a bloodwork test, for example according to Equation (1):

$$homaIR = \frac{\left[ glucose\ in\ \frac{mmol}{L} \right] \times \left[ insulin\ in\ \frac{mmol}{L} \right]}{22.5} \quad \text{Eq. (1)}$$

The derived feature "tghdlratio" represents a ratio of triglycerides to high density lipoproteins in the blood, which may be interpreted as a proxy for insulin resistance. The feature "tghdlratio" may be calculated, for example according to Equation (2):

$$tghdlratio = \frac{triglycerides\ in\ mg/dL}{HDL\ cholesterol\ in\ mg/dL}$$

The derived feature "tgglucindex" represents to a result of applying a logarithmic function to a product of triglycerides and fasting glucose levels, which is a value related to insulin resistance. The feature "tgglucindex" may be calculated for example according to Equation (3):

$$tgglucindex = \log\ \log\ \left( triglycerides\ in\ \frac{mg}{dL} \times glucose\ in\ \frac{mg}{dL} \right) \quad \text{Eq. (3)}$$

The feature "measured_homaIR" is a Boolean value indicating whether the "homaIR" value was measured for a particular day or if it was forward-filled from a previous measurement. Similarly, the features "measured_tghdlratio" and "measured_tgglucindex" are Boolean values indicating whether those metrics were measured on a particular day, or if they were forward-filled.

The derived feature "glucscore" is a score that digitally represents a patient's glucose level. In one embodiment, a "glucscore" of 0 represents a 3-day mean glucose level below 125 mg/dL. A "glucscore" of 1 represents a mean glucose level between 125 and 137 mg/dL. A "glucscore" of 2 represents a mean glucose level between 137 and 145 mg/dL. A "glucscore" of 3 represents a mean glucose level between 145 and 160 mg/dL. A "glucscore" of 4 represents a mean glucose level between 160 and 200 mg/dL. A "glucscore" of 5 represents a mean glucose level greater than 200 mg/dL. In other embodiments, the long-term prediction module 825 may define additional or fewer scores representing different or varying ranges of glucose levels to represent a patient's glucose levels at various granularities.

The derived feature "ketscore" is a score that digitally represents a patient's Beta-hydroxybutyrate (BHB) level. In one embodiment, a "ketscore" of 1 represents a BHB level less than 0.4 mM, a "ketscore" of 1 corresponds to a BHB level between 0.4 and 0.7 mM, a "ketscore" of 2 represents a BHB level between 0.7 and 1.2 mM, a "ketscore" of 3 corresponds to a BHB level between 1.2 and 2.0 mM, a "ketscore" of 4 corresponds to a BHB level between 2.0 and 3.0 mM, a "ketscore" of 5 corresponds to a BHB level between 3.0 and 4.0 mM, and a "ketscore" of 6 corresponds to a BHB level greater than 4.0 mM. In other embodiments, the long-term prediction module 825 may define additional or fewer scores representing different or varying ranges of glucose levels to represent a patient's glucose levels at various granularities.

The derived feature "cpepcgm" is a product of the glucose level in the blood (mg/dL) and the C-peptide level in the blood (ng/mL), which is representative of insulin resistance. C-peptide is a marker of endogenous insulin product and has a longer half-life than insulin itself but is insensitive to exogenous insulin. The measurement of the glucose level in the blood may be an average of the glucose reported by a continuous glucose monitor over the 2 hours prior to a blood draw from which the C-peptide level is measured. The feature "cpepcgm" may be calculated, for example according to Equation (4):

$$cpepcgm = \left[\text{mean glucose in } \frac{mg}{dL}\right] \times \qquad \text{Eq. (4)}$$
$$\left[C - \text{peptide conentration in } \frac{ng}{mL}\right]$$

The derived feature "hgp_score" represents the incremental Area Under the Curve (AUC) of a glucose spike (h*mg/dL), which measured at least five hours after the patient's last mean and while the patient is sleeping. Accordingly, any glucose spikes can be attributed to hepatic glucose production rather than digested food.

The feature "glucose_ketone_index" is a comparison of the "glucscore" described above and the "ketscore" described above. The "glucose_ketone_index" models the relationship between a patient's glucose levels and their BHB levels. In a healthy patient, BHB levels and glucose levels are inversely related. Accordingly, the values for the "glucose_ketone_index" can be determined based on the "glucscore" and the "ketscore" according to Table 2.

TABLE 2

Illustrative Interpretation of "Glucose_Ketone_Index"

| | | ketscore | | | | | | |
| --- | --- | --- | --- | --- | --- | --- | --- | --- |
| | | 0 | 1 | 2 | 3 | 4 | 5 | 6 |
| glucscore | 0 | 5 | 5 | 5 | 5 | 2 | 2 | 5 |
| | 1 | 5 | 5 | 5 | 5 | 2 | 2 | 2 |
| | 2 | 4 | 4 | 2 | 2 | 2 | 2 | 1 |
| | 3 | 3 | 3 | 2 | 2 | 2 | 1 | 1 |
| | 4 | 3 | 3 | 1 | 1 | 1 | 1 | 1 |
| | 5 | 1 | 1 | 1 | 1 | 1 | 1 | 1 |

In one embodiment, each of the systolic BP prediction submodel 840 and the diastolic BP prediction submodel 845 implement a long-short term memory recurrent neural network (LSTM) with GRU cells (e.g., LSTM and GRU layers from the Tensorflow library) to process sequential features into a diastolic BP predictions and systolic BP predictions, respectively. LSTM and GRU cells are variants of recurrent neural networks that allow for the training of models capable of learning over long sequences of time variant data.

As described with reference to FIG. 6, the systolic BP prediction submodel 840 and the diastolic BP prediction submodel each train a baseline LSTM using a training dataset of data from a population of patients. Next, each of the submodels 840 and 845 train a personalized LSTM by retraining the baseline LSTM model using a training dataset of exclusively the patient's own data. Accordingly, the weights of each personalized LSTM model are initialized using the trained weights from the baseline LSTM, such that the personalized LSTM represents a variation of the baseline LSTM that is fine-tuned based on the patient's own data. For embodiments in which sequential features are divided into three-day intervals, a label assigned to each interval describing a diastolic BP measurement and a systolic BP measurement recorded during the three days.

Each GRU cell in the personalized LSTM model implemented by the systolic BP prediction submodel 840 and the personalized LSTM model implemented by the diastolic BP prediction submodel represents a subset of the sequential features (e.g., sequential features recorded during a three day interval), such that each of the submodels 840 and 845 iteratively process sequential features recorded over a time period to output a blood pressure prediction for the corresponding interval.

In one embodiment, each of the systolic BP prediction submodel 840 and the diastolic BP prediction submodel 845 implement a neural network with Dense layers (e.g., a Dense neural network from the Tensorflow library) to process the static features described above. The Dense neural network implemented by the submodels 840 and 845 receive, as inputs, static features measured or derived from a patient's most recent lab tests to generate a static blood pressure prediction. As described with reference to FIG. 6, a baseline Dense neural network is trained using a training dataset of data from a population of patients. Next, a personalized Dense neural network is generated by retraining the baseline Dense neural network using a training dataset of exclusively the patient's own data. Accordingly, the weights of the personalized Dense neural network are initialized using the trained weights from the Dense neural network, such that the personalized Dense neural network represents a variation of the baseline Dense neural network that is fine-tuned based on the patient's own data.

In one embodiment, the models implemented by both the systolic BP prediction submodel 840 and the diastolic BP prediction submodel 845 are trained based on a two thirds of a patient's personalized training dataset and evaluated based on the remaining third of the patient's personalized training dataset.

The systolic BP prediction submodel 840 concatenates the systolic blood pressure prediction outputted by the first model trained to process sequential features (e.g., the LSTM model described above) with the systolic blood pressure prediction outputted by the second model trained to process static features (e.g., Dense neural network described above) to generate an aggregate prediction of a patient's rolling systolic blood pressure average, for example their rolling average over a 3-day time period. Similarly, the diastolic blood pressure prediction submodel 845 concatenates the diastolic blood pressure prediction outputted by model trained to process sequential features (e.g., the LSTM model described above) with the diastolic blood pressure prediction outputted by the second model trained to process static features (e.g., Dense neural network) to generate an aggregate prediction of a patient's rolling diastolic blood pressure average, for example their rolling average over a 3-day time period. The concatenation performed by each of the systolic BP prediction submodel 840 and the diastolic BP prediction submodel 845 is further described with reference to FIG. 8C. In practice, the long-term prediction model 830 generates predictions of systolic blood pressure with a mean absolute error (MAE) of 4.3 mmHg and the diastolic blood pressure with an MAE of 3.5 mmHg.

In a first implementation directed towards non-hypertensive patients, the blood pressure twin module 520 does not evaluate nutrition data reported from a patient. Instead, the blood pressure twin module 520 evaluates passively recorded biosignals for the patient to perform long-term health monitoring and prevention of hypertension. In such an embodiment, the blood pressure twin module 520 inputs the passively recorded biosignals to the long-term prediction model 825, which generates a long-term prediction of the patient's systolic and diastolic blood pressure using the systolic BP prediction submodel 840 and the diastolic BP prediction submodel 845.

In a second implementation directed towards hypertensive patients, the blood pressure twin module 520 receives nutrition data reported by a patient in addition to the passively recorded sensor data and lab test data. The addition of the actively recorded nutrition data to the passively recorded sensor data and lab test data enables the blood pressure twin module 520 to monitor the patient's blood pressure dynamic at a more granular level. In this implementation, the blood pressure twin module 520 implements the short-term blood pressure prediction model 810 and the long-term prediction model 830 in combination to generate an ensemble prediction that is more accurate than the blood pressure predictions of either model individually. The ensemble prediction offsets the biases of each of the short-term prediction model 810 and the long-term prediction model 830 to reduce the overall error in the predicted blood pressure, for example according to Equation (5):

$$P_{ensemble} = rP_{LTP} + (1 - r)P_{STP}$$

where r is a value between 0 and 1 which represents the relative strength of the prediction by the long-term prediction model 825. In embodiments where both predictions are higher than r or both predictions are lower than r, the ensemble prediction minimizes extreme errors in the predictions generated by either model. Similarly, in embodiments where one prediction is higher than r and the other is lower than r, the ensemble prediction is more accurate than predictions generated by either model individually. In some embodiments, the value of r is defined as 0.43. In practice, the ensemble prediction achieved a systolic MAE of 3.7 mmHg and a diastolic MAE of 2.6 mmHg, when using an exponentially weighted moving average of blood pressure with a half-life of 3 days as a reference.

Figure 8B:
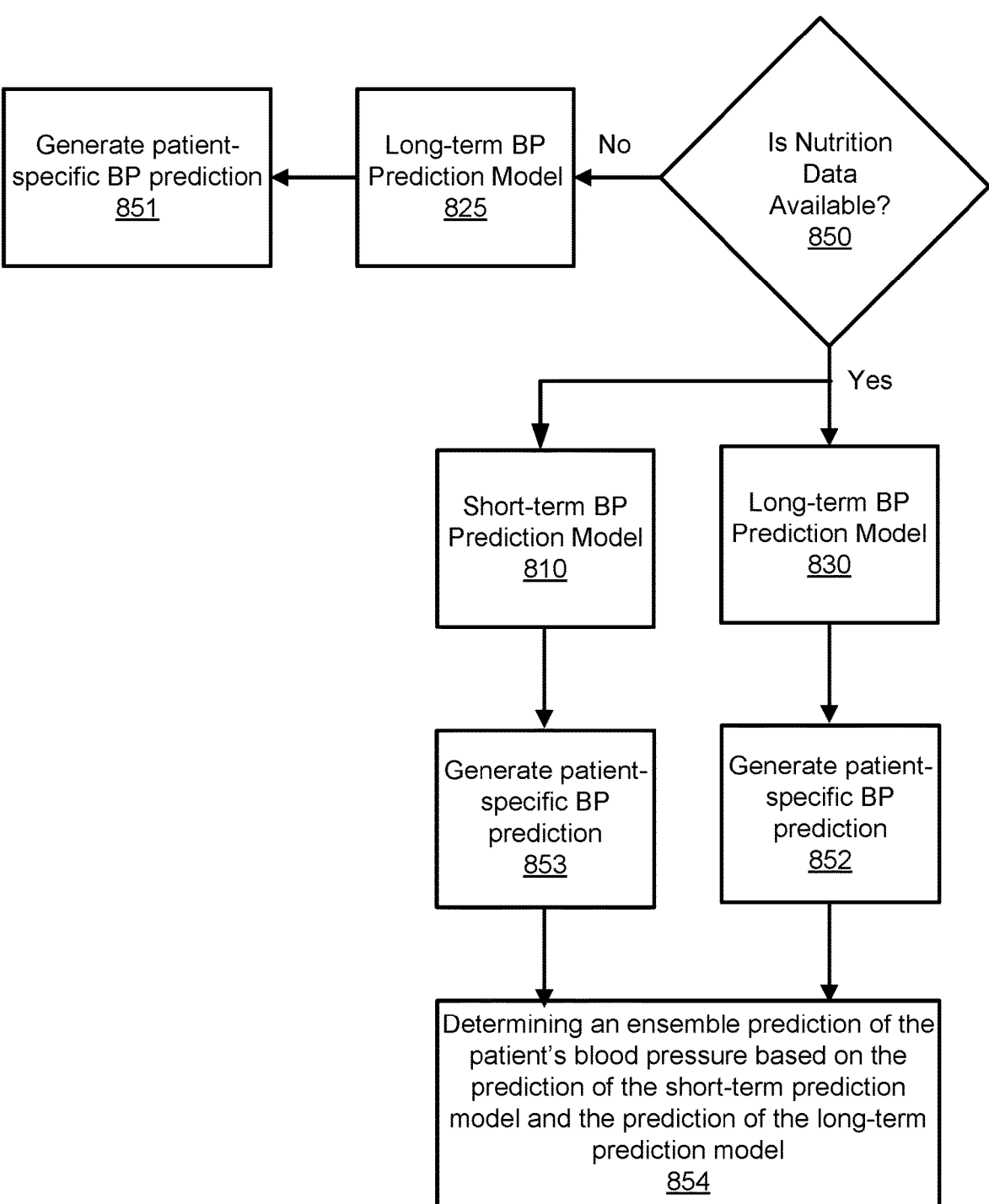
FIG. 8B is a flowchart illustrating a process for determining a prediction of blood pressure levels for a patient, according to one embodiment.

FIG. 8B is a flowchart illustrating a process for determining a prediction of blood pressure levels for a patient, according to one embodiment. The blood pressure twin module 520 determines 850 whether nutrition data was reported by the patient during a current time period. If nutrition data is not available, the blood pressure twin module 520 encodes biosignals passively recorded during that time period into a vector representation and inputs the encoded vector representation to the long-term BP prediction model 825 which generates 851 a long-term prediction of the patient's systolic blood pressure and diastolic blood pressure.

If the patient did report nutrition data during the current time period, the blood pressure twin module 520 encodes the reported nutrition data and the passively recorded biosignals into a vector representation and inputs the encoded vector representation to a short-term prediction model 810, which generates 853 daily predictions of the patient's systolic and diastolic blood pressure. Additionally, the blood pressure twin module 520 inputs the passively recorded biosignals to the long-term prediction model 825, which generates 852 predictions of the patient's systolic and diastolic blood pressure over a longer time period, for example a time period that began before current day. The blood pressure twin module 520 determines 854 a highly accurate ensemble prediction of both the patient's systolic and diastolic blood pressure by combining the daily predictions generated by the short-term prediction model 810 and the long-term predictions generated by the long-term prediction model 830.

Figure 8C:
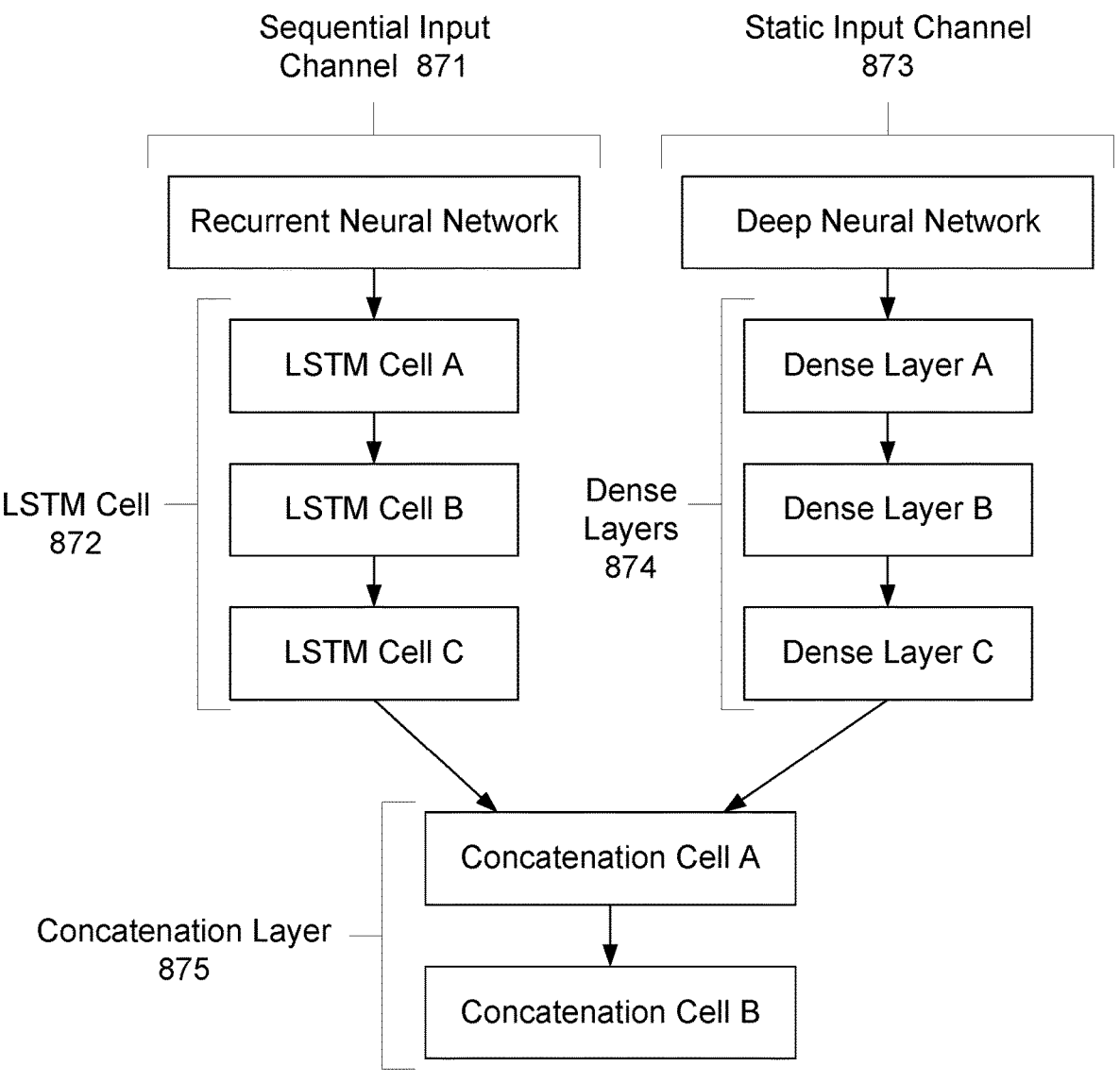
FIG. 8C is an illustration of a flowchart for concatenating a blood pressure prediction generated based on sequential features with a blood pressure prediction generated based on static features, according to one embodiment.

FIG. 8C is an illustration of a flowchart for concatenating a blood pressure prediction (either systolic or diastolic blood pressure) generated based on sequential features with a blood pressure prediction (either systolic or diastolic blood pressure) generated based on static features, according to one embodiment. The techniques discussed herein with reference to FIG. 8C may be employed by any submodel implemented by the long-term prediction model 830, for example the systolic BP prediction submodel 840 and the diastolic BP prediction submodel 845. As discussed above, the long-term prediction module 830 implements a deep neural network 870 with multiple, jointly-trained input channels to generate predictions of a patient's blood pressure levels based on a combination of sequential and static input features. The multiple channels enable the long-term prediction model to process particular types of input feature (e.g., a sequential input feature or a static input feature).

A first input channel 871 of the deep neural network generates a sequential blood pressure estimation by passing sequential data through a series of recurrent neural network layers, for examples LSTM cells 872. As discussed above, LSTM cells 872 are specialized components capable of modeling complex sequential dynamics present in biometric data. This first input channel 871 may be implemented in a flexible fashion that enables a submodel of the long-term prediction model 830 (e.g., the systolic BP prediction submodel 840 and the diastolic BP prediction submodel 845) to accommodate input sequences of varying lengths. A second input channel 873 of the deep neural network generates a static blood pressure estimation by passing static data through a stack of standard dense layers 874 of the neural network. In one embodiment, each dense layer 874 comprises 64 neurons.

The first input channel 871 and the second input channel 873 converge at a concatenation layer 873 of the deep neural network, where the submodel of the long-term prediction model 830 combines the signals from the two input channels into an aggregate estimate of a patient's blood pressure. The submodel of the long-term prediction model 830 passes the aggregated estimate through a series of dense, fully connected layers to determine the combination of information gained from each of the two input channels that will yield the most or most relevant insight into a patient's metabolic state.

IV.E Patient-Specific Recommendations

The recommendation module 360 may include a combination of rule-based artificial intelligence techniques representing codified medical knowledge from established medical practice (e.g., American Diabetes Association guidelines, research literature, and insights gained from past medical treatments). The recommendation module 360 applies the codified knowledge in an automated manner to recommend treatments for new patients using the patient health management platform 130.

The platform 130 additionally categorizes patients into a cohort with other patients with similar metabolic profiles. The recommendation module 360 applies a system of rule to assign patients with a similar metabolic profile to the same cohort. The recommendation module 360 then tailors a specific treatment recommendation (i.e., a combination of nutrition and medication regimens) for the metabolic profiles of patients in each cohort. In some implementations, the recommendation module 360 generates a representative metabolic profile for each cohort based on an average of the metabolic profiles for each patient in cohort or an aggregate of the metabolic profiles for each patient in cohort. The rule-based intelligence applied to categorize patients in cohorts is based on biosignals characterizing a patient's metabolic state or general health, for example biosignals recorded by wearable sensors or measured using lab tests. Specific examples of such cohorting rules include, but are not limited to, BMI, 5-day average blood glucose ("5DG"), 5-day average of grams of net carbs eaten per day ("5dgnc"), 5-day average of the number of >50 mg/dL blood glucose spikes per day ("5dspike"), ketone levels, and whether the patient is taking medications like glimepiride.

V. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of the above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A method for predicting a blood pressure level of a patient, the method comprising:

accessing, by a health management platform from a data store, a plurality of biosignals recorded for the patient, the plurality of biosignals comprising one or more of: 1) sensor data collected during a time period by one or more wearable sensors worn by the patient, and 2) lab test data collected during the time period;

encoding the 1) sensor data and 2) lab test data into a vector representation, the vector representation comprising static features and sequential features, wherein a static feature represents biological data collected at a single point in time, a sequential feature represents biological data collected at multiple points during the time period and includes a time dependent variable, and the encoding comprises:

dividing the sequential feature based on a set of time intervals, and for each sequential feature, labelling the sequential feature to define (1) a time interval from the set of time intervals and (2) a diastolic blood pressure measurement in the time interval, and (3) a systolic blood pressure measurement in the time interval;

applying a long-term prediction model to the vector representation to generate a prediction of the blood pressure of the patient over the time period, the long term prediction model generating the prediction by:

determining a sequential blood pressure estimation by passing sequential input data through a series of recurrent neural network layers, the recurrent neural network layers:

determining a long-term diastolic blood pressure prediction for the patient during the time period based on the vector representation; and determining a long-term systolic blood pressure prediction for the patient during the time period based on the vector representation;

determining a static blood pressure estimation by passing static input data through a stack of dense neural network layers, the dense neural network layers:

determining a static blood pressure prediction the patient during the time period based on the vector representation; and concatenating the static blood pressure estimation and the sequential blood pressure estimation in neural network layers to determine the prediction of the blood pressure of the patient over the time period;

wherein the long-term prediction model is trained based on a training dataset of true blood pressure measurements recorded for the patient during an initialization period and historical biosignals recorded for the patient that contributed to each true blood pressure measurement; and generating, for display on a mobile device, a notification describing the long-term diastolic blood pressure prediction and the long-term systolic blood pressure prediction determined for the patient.

2. The method of claim 1, wherein training the long-term prediction model further comprises:

training a baseline model to generate a blood pressure prediction based on a training dataset of sensor data and lab test data collected for a population of patients;

generating a patient-specific training dataset by compiling true blood pressure measurements recorded for the patient during the initialization period and historical biosignals recorded for the patient that contributed to each true blood pressure measurement; and generating and iteratively training the long-term prediction model by applying the baseline model to the patient-specific training dataset.

3. The method of claim 1, further comprising:

modifying a digital representation of a metabolic state of the patient based on the long-term diastolic blood pressure prediction and the long-term systolic blood pressure prediction determined for the patient.

4. The method of claim 1, further comprising:

receiving, from a mobile device of the patient, a report of food items consumed by the patient on a current day during the time period;

accessing, from a storage device of a remote server, nutrition data of the reported food items;

encoding the accessed nutrition data, sensor data, and lab test data into a second vector representation;

applying a short-term prediction model to the second vector representation to generate a prediction of the blood pressure of the patient during the current day, wherein the short-term prediction model is trained based on a training dataset of true blood pressure measurements recorded for the patient during the initialization period and historical biosignals corresponding to biosignals encoded into the second vector representation that contributed to each true blood pressure measurement and, to:

determine a short-term diastolic blood pressure prediction for the patient during the current day based on a first vector representation; and determine a short-term systolic blood pressure prediction for the patient during current day based on the first vector representation.

5. The method of claim 4, further comprising:

training a baseline model to generate a short-term blood pressure prediction based on a training dataset of sensor data and lab test data collected for a population of patients;

generating a short-term patient-specific training dataset by compiling true blood pressure measurements recorded for the patient during the initialization period and historical biosignals recorded for the patient that contributed to each true blood pressure measurement;

generating and iteratively training the short-term prediction model by applying the baseline model to the short-term patient-specific training dataset.

6. The method of claim 4, further comprising:

determining 1) an ensemble diastolic blood pressure measurement for the patient during the current day based diastolic blood pressure prediction generated by each of the short-term prediction model and the long-term prediction model, and 2) an ensemble systolic blood pressure measurement for the patient during the current day based on the systolic blood pressure prediction generated by each of the short-term prediction model and the long-term prediction model; and generating, for display on the mobile device, a notification describing the ensemble diastolic blood pressure measurement and ensemble systolic blood pressure measurement determined for the patient.

7. The method of claim 1, further comprising:

classifying the patient into a category defined by the American Heart Association based on the long-term diastolic blood pressure prediction and the long-term systolic blood pressure prediction determined for the patient, wherein the categories include:

normal blood pressure;
elevated blood pressure;
high blood pressure stage 1;
high blood pressure stage 2; and
hypertensive.

8. The method of claim 7, further comprising:

responsive to classifying the patient as hypertensive, generating a request and user interface for the patient to report food consumed on each day of the time period; and for each day of the time period, transmitting the request and user interface for display on a mobile device of the patient.

9. A non-transitory computer readable medium storing instructions for predicting a blood pressure level of a patient encoded thereon that, when executed by a processor, cause the processor to:

access, by a health management platform from a data store, a plurality of biosignals recorded for the patient, the plurality of biosignals comprising one or more of: 1) sensor data collected during a time period by one or more wearable sensors worn by the patient, and 2) lab test data collected during the time period;

encode the 1) sensor data and 2) lab test data into a vector representation, the vector representation comprising static features and sequential features, wherein a static feature represents biological data collected at a single point in time, a sequential feature represents biological data collected at multiple points during the time period and includes a time dependent variable, and the encoding comprises:

dividing the sequential feature based on a set of time intervals, and for each sequential feature, labelling the sequential feature to define (1) a time interval from the set of time intervals and (2) a diastolic blood pressure measurement in the time interval, and (3) a systolic blood pressure measurement in the time interval;

apply a long-term prediction model to the vector representation to generate a prediction of the blood pressure of the patient over the time period, the long term prediction model generating the prediction by:

determining a sequential blood pressure estimation by passing sequential input data through a series of recurrent neural network layers, the recurrent neural network layers:

determining a long-term diastolic blood pressure prediction for the patient during the time period based on the vector representation; and determining a long-term systolic blood pressure prediction for the patient during the time period based on the vector representation;

determining a static blood pressure estimation by passing static input data through a stack of dense neural network layers, the dense neural network layers:

determining a static blood pressure prediction the patient during the time period based on the vector representation; and concatenating the static blood pressure estimation and the sequential blood pressure estimation in neural network layers to determine the prediction of the blood pressure of the patient over the time period;

wherein the long-term prediction model is trained based on a training dataset of true blood pressure measurements recorded for the patient during an initialization period and historical biosignals recorded for the patient that contributed to each true blood pressure measurement; and generate, for display on a mobile device, a notification describing the long-term diastolic blood pressure prediction and the long-term systolic blood pressure prediction determined for the patient.

10. The non-transitory computer readable medium of claim 9, wherein the instructions for training the long-term prediction further cause the processor to:

train a baseline model to generate a blood pressure prediction based on a training dataset of sensor data and lab test data collected for a population of patients;

generate a patient-specific training dataset by compiling true blood pressure measurements recorded for the patient during the initialization period and historical biosignals recorded for the patient that contributed to each true blood pressure measurement; and generate and iteratively training the long-term prediction model by applying the baseline model to the patient-specific training dataset.

11. The non-transitory computer readable medium of claim 9, further comprising instructions that cause the processor to:

modify a digital representation of a metabolic state of the patient based on the long-term diastolic blood pressure prediction and the long-term systolic blood pressure prediction determined for the patient.

12. The non-transitory computer readable medium of claim 9, further comprising instructions that cause the processor to:

receive, from a mobile device of the patient, a report of food items consumed by the patient on a current day during the time period;

access, from a storage device of a remote server, nutrition data of the reported food items;

encode the accessed nutrition data, sensor data, and lab test data into a second vector representation;

apply a short-term prediction model to the second vector representation to generate a prediction of the blood pressure of the patient during the current day, wherein the short-term prediction model is trained based on a training dataset of true blood pressure measurements recorded for the patient during the initialization period and historical biosignals corresponding to biosignals encoded into the second vector representation that contributed to each true blood pressure measurement and, to:

determine a short-term diastolic blood pressure prediction for the patient during the current day based on a first vector representation; and determine a short-term systolic blood pressure prediction for the patient during current day based on the first vector representation.

13. The non-transitory computer readable medium of claim 12, further comprising instructions that cause the processor to:

train a baseline model to generate a short-term blood pressure prediction based on a training dataset of sensor data and lab test data collected for a population of patients;

generate a short-term patient-specific training dataset by compiling true blood pressure measurements recorded for the patient during the initialization period and historical biosignals recorded for the patient that contributed to each true blood pressure measurement;

generate and iteratively training the short-term prediction model by applying the baseline model to the short-term patient-specific training dataset.

14. The non-transitory computer readable medium of claim 12, further comprising instructions that cause the processor to:

determine 1) an ensemble diastolic blood pressure measurement for the patient during the current day based diastolic blood pressure prediction generated each of the short-term prediction model and the long-term prediction model, and 2) an ensemble systolic blood pressure measurement for the patient during the current day based on the systolic blood pressure prediction generated by each of the short-term prediction model and the long-term prediction model; and generate, for display on the mobile device, a notification describing the ensemble diastolic blood pressure measurement and ensemble systolic blood pressure measurement determined for the patient.

15. The non-transitory computer readable medium of claim 9, further comprising instructions that cause the processor to:

classify the patient into a category defined by the American Heart Association based on the long-term diastolic blood pressure prediction and the long-term systolic blood pressure prediction determined for the patient, wherein the categories include:

normal blood pressure;

elevated blood pressure;

high blood pressure stage 1;

high blood pressure stage 2; and hypertensive.

16. The non-transitory computer readable medium of claim 15, wherein the instructions further cause the processor to:

responsive to classifying the patient as hypertensive, generate a request and user interface for the patient to report food consumed on each day of the time period; and for each day of the time period, transmit the request and user interface for display on a mobile device of the patient.

17. A system comprising:

one or more processors; and a non-transitory computer readable medium storing instructions for predicting a blood pressure level of a patient encoded thereon that, when executed by a processor, cause the processor to:

access, by a health management platform from a data store, a plurality of biosignals recorded for the patient, the plurality of biosignals comprising one or more of: 1) sensor data collected during a time period by one or more wearable sensors worn by the patient, and 2) lab test data collected during the time period;

encode the 1) sensor data and 2) lab test data into a vector representation, the vector representation comprising static features and sequential features, wherein a static feature represents biological data collected at a single point in time, a sequential feature represents biological data collected at multiple points during the time period and includes a time dependent variable, and the encoding comprises:

dividing the sequential feature based on a set of time intervals, and for each sequential feature, labelling the sequential feature to define (1) a time interval from the set of time intervals and (2) a diastolic blood pressure measurement in the time interval, and (3) a systolic blood pressure measurement in the time interval;

apply a long-term prediction model to the vector representation to generate a prediction of the blood pressure of the patient over the time period, the long term prediction model generating the prediction by:

determining a sequential blood pressure estimation by passing sequential input data through a series of recurrent neural network layers, the recurrent neural network layers:

determining a long-term diastolic blood pressure prediction for the patient during the time period based on the vector representation; and determining a long-term systolic blood pressure prediction for the patient during the time period based on the vector representation;

determining a static blood pressure estimation by passing static input data through a stack of dense neural network layers, the dense neural network layers:

determining a static blood pressure prediction the patient during the time period based on the vector representation; and concatenating the static blood pressure estimation and the sequential blood pressure estimation in neural network layers to determine the prediction of the blood pressure of the patient over the time period;

wherein the long-term prediction model is trained based on a training dataset of true blood pressure measurements recorded for the patient during an initialization period and historical biosignals recorded for the patient that contributed to each true blood pressure measurement; and generate, for display on a mobile device, a notification describing the long-term diastolic blood pressure prediction and the long-term systolic blood pressure prediction determined for the patient.

* * * * *